(12) United States Patent
Mayolet et al.

(10) Patent No.: US 6,894,284 B2
(45) Date of Patent: May 17, 2005

(54) UV OPTICAL FLUORIDE CRYSTAL ELEMENTS FOR λ < 200NM LASER LITHOGRAPHY AND METHODS THEREFOR

(75) Inventors: Alexandre M. Mayolet, Auneau (FR); Michael A. Pell, Singapore (SG); Nikolay T. Timofeev, St. Petersburg (RU)

(73) Assignee: Corning Incorporated, Corning, NY (US)

( * ) Notice: Subject to any disclaimer, the term of this patent is extended or adjusted under 35 U.S.C. 154(b) by 178 days.

(21) Appl. No.: 10/317,789

(22) Filed: Dec. 11, 2002

(65) Prior Publication Data

US 2003/0160177 A1 Aug. 28, 2003

(30) Foreign Application Priority Data

Dec. 13, 2001 (FR) .......................................... 01 16097
Aug. 12, 2002 (RU) ...................................... 2002121258

(51) Int. Cl.$^7$ .......................... C30B 11/00; G02B 1/02
(52) U.S. Cl. .................................... 250/372; 250/474.1
(58) Field of Search ............................ 250/372, 474.1, 250/484.5; 359/355; 501/151; 376/247; 252/588; 117/940; 355/53

(56) References Cited

U.S. PATENT DOCUMENTS

| | | | |
|---|---|---|---|
| 6,226,128 B1 | 5/2001 | Shiozawa | 359/642 |
| 6,377,332 B1 | 4/2002 | Sakuma | 355/53 |
| 6,395,657 B2 * | 5/2002 | Mayolet et al. | 501/3 |
| 6,630,117 B2 * | 10/2003 | Sparrow | 423/490 |
| 2001/0046091 A1 * | 11/2001 | Mayolet et al. | 359/722 |
| 2002/0132719 A1 * | 9/2002 | Mayolet et al. | 501/3 |
| 2004/0026631 A1 * | 2/2004 | Mayolet et al. | 250/461.1 |
| 2004/0115485 A1 * | 6/2004 | Mayolet et al. | 428/698 |

FOREIGN PATENT DOCUMENTS

WO          WO01/86032 A1     11/2001

* cited by examiner

Primary Examiner—Otilia Gabor
(74) Attorney, Agent, or Firm—Walter M. Douglas

(57) ABSTRACT

This invention provides a method of detecting sub-ppm lead impurity levels in a below 200 nm transmitting optical calcium flouride crystal. The method includes providing a below 200 nm wavelength transmitting optical flouride crystal having a crystal light transmission path length, providing a 200–210 nm spectrophotometer having a light source for producing a transmission test wavelength in the range 200 to 210 nm and a transmission detector for measuring transmission of the test wavelength, and transmitting the transmission test wavelength in the range of 200 to 210 nm through the below 200 nm wavelength transmitting optical flouride light transmission path length and measuring the transmission of the 200 to 210 nm test wavelength through the path length to provide a lead ppb impurity level measurement less than 500 ppb. The invention provides for improved manufacturing of below 200 nm wavelength optical elements and optical fluoride crystals such as ultralow lead contaminated calcium flouride.

33 Claims, 18 Drawing Sheets

UV OPTICAL FLUORIDE CRYSTAL ELEMENTS FOR λ < 200NM LASER LITHOGRAPHY AND METHODS THEREFOR

RELATED APPLICATIONS

This application claims the benefit of French Patent Application, Serial Number 01 16097, filed Dec. 13, 2001 entitled UV OPTICAL FLUORIDE CRYSTAL ELEMENTS FOR <200 NM LASER LITHOGRAPHY AND METHODS THEREFOR.

This application also claims the benefit of Russian Patent Application, Serial Number RU2002121258, filed Aug. 12, 2002, entitled UV OPTICAL FLUORIDE CRYSTAL ELEMENTS FOR <200 NM LASER LITHOGRAPHY AND METHODS THEREFOR.

BACKGROUND OF THE INVENTION

The present invention relates generally to λ<200 nm transmitting optical fluoride crystals and optical elements therefrom, and particularly to testing and making high quality optical fluoride crystals and lithography/laser elements with high fluoride purity and very low lead and oxygen contaminant levels.

The burden of the demands for improved performance of computers falls on the lithographic process used to fabricate the integrated circuit chips. Lithography involves irradiating a mask and focusing the pattern of this mask through an optical microlithography system onto a wafer coated with a photoresist. The pattern on the mask is thereby transferred onto the wafer. Decreasing the line-widths of the features on a given wafer brings about advances in performance. The enhanced resolution required to achieve finer line-widths is enabled by decreasing the wavelength of the illumination source. The energies used in lithographic patterning are moving deeper into the UV region. Optical components capable of reliable performance at these short optical microlithography wavelengths are required. Few materials are known that have a high transmittance at 193 nm and 157 nm and do not deteriorate under intense laser exposure. Fluoride crystals such as calcium fluoride and barium fluoride are potential materials with high transmittance at wavelengths <200 nm. Projection optical photolithography systems that utilize the vacuum ultraviolet wavelengths of light at and below 193 nm provide desirable benefits in terms of achieving smaller feature dimensions. Microlithography systems that utilize vacuum ultraviolet wavelengths in the 157 nm wavelength region have the potential of improving integrated circuits and their manufacture. The commercial use and adoption of 193 nm and below vacuum ultraviolet wavelengths such as 157 nm has been hindered by the transmission nature of such deep ultraviolet wavelengths in the 157 nm region through optical materials. Such slow progression by the semiconductor industry of the use of VUV light below 175 nm such as the 157 nm region light has been also due to the lack of economically manufacturable blanks from optically transmissive materials and difficulties in manufacturing blanks which can be identified as high quality and qualified for their intended microlithography optical element and laser use. For the benefit of deep ultraviolet photolithography in the VUV 157 nm region such as the emission spectrum of the fluorine excimer laser to be utilized in the manufacturing of integrated circuits there is a need for below 200 nm wavelength transmitting optical fluoride crystals that have beneficial optical and highly qualified properties including good transmission below 200 nm and at 193 nm and 157 nm and that can be manufactured, tested, evaluated, measured and qualified for use economically. The present invention overcomes problems in the prior art and provides a means for economically providing high quality measured very low lead contaminant levels for below 200 nm wavelength transmitting optical fluoride crystals that can be used to improve the manufacturing of integrated circuits with vacuum ultraviolet wavelengths. The invention provides for absorption band analysis testing of high quality calcium fluoride optical fluoride crystal lithography and excimer laser elements with very low lead contaminant levels.

SUMMARY OF THE INVENTION

The invention includes a method of detecting a low lead impurity level in a below 200 nm transmitting optical fluoride crystals. The method includes providing a below 200 nm wavelength transmitting optical fluoride crystal having a crystal light transmission path length ≧2 mm. The method includes providing a light transmission 200–210 nm scanning spectrophotometer having a light source for producing transmission test wavelengths in the range 200 to 210 nm and a transmission detector for measuring transmission of the test wavelengths and then transmitting the 200 to 210 nm range transmission test wavelengths through the below 200 nm wavelength transmitting optical fluoride crystal light transmission path length and measuring the transmission of the 200 to 210 nm test wavelengths through the path length to provide a lead ppb impurity level measurement less than 900 ppb. Preferably the invention provides a lead ppb impurity level measurement less than 500 ppb, more preferred 300 ppb, more preferred 100 ppb, more preferred 50 ppb, more preferred 20 ppb, and most preferred 10 ppb.

The invention includes a method of measuring below 1 ppm lead impurity levels in an optical fluoride lithography crystal for transmitting below 200 nm wavelengths of light. The method includes providing a below 200 nm wavelength transmitting optical fluoride crystal having a crystal light transmission path length ≧1 cm. The method includes providing a 200–210 nm absorption band measurement system spectrophotometer having a light source for producing a test wavelength in the range 200 to 210 nm and a transmission detector for calculating an absorption coefficient at the test wavelength, transmitting the test wavelengths in the range 200 to 210 nm through the below 200 nm wavelength transmitting optical fluoride crystal light transmission ≧1 cm path length and measuring the absorption coefficient at the test wavelengths through the ≧1 cm path length to provide a lead contaminant level absorption coefficient <0.0017 $cm^{-1}$.

The invention includes a method of making a below 200 nm wavelength optical lithography element. The method includes providing a below 200 nm wavelength transmitting optical fluoride crystal having a crystal light transmission path length ≧2 mm and providing a light transmission 200–210 nm spectrophotometer measurement system having a light source for producing a transmission test wavelength in the range 200 to 210 nm and a transmission detector for measuring transmission of the test wavelength. The method includes transmitting the transmission test wavelength in the range 200 to 210 nm through the below 200 nm wavelength transmitting optical fluoride crystal light transmission path length and measuring the transmission of the 200 to 210 nm test wavelength through the path length to provide a contaminant level measurement less than 500 ppb, preferably less than 300 ppb, more preferably less than 100 ppb and then forming the optical fluoride crystal into a below 200 nm wavelength optical element having an absorption coefficient at 200 to 210 nm<0.0017 cm$^{-1}$.

The invention includes a method of making a below 200 nm wavelength transmitting optical fluoride crystal. The method includes providing a premelt calcium fluoride crystal solid. The method includes melting the premelt calcium fluoride crystal solid to form a calcium fluoride melt and growing a calcium fluoride crystal from the melt to provide an optical calcium fluoride crystal for transmitting below 200 nm wavelengths. The method includes providing a light transmission 200–210 nm spectrometer having a light source for producing a transmission test wavelength in the range 200 to 210 nm and a transmission detector for measuring transmission of the test wavelength and measuring a lead contaminant level in a path length of the calcium fluoride with the transmission test wavelength in the range 200 to 210 nm, with the grown optical calcium fluoride crystal for transmitting below 200 nm wavelengths having an absorption coefficient at 200 to 210 nm<0.0017 cm$^{-1}$. The invention includes a below 200 nm wavelength transmitting optical fluoride crystal of calcium fluoride having a below 200 nm transmission greater than 99%/cm and a lead ppb level less than 50 and an absorption coefficient at 200 to 210 nm<0.0017 cm$^{-1}$.

The invention includes a method of making a below 200 nm wavelength transmitting optical fluoride crystal. The method includes providing a premelt barium fluoride crystal solid, melting the premelt barium fluoride crystal solid to form a barium fluoride melt and growing a barium fluoride crystal from the melt to provide an optical barium fluoride crystal for transmitting below 200 nm wavelengths. The method includes providing a light transmission 200–210 nm spectrometer having a light source for producing a transmission test wavelength in the range 200 to 210 nm and a transmission detector for measuring transmission of the test wavelength and measuring a lead contaminant level in a path length of the barium fluoride with said transmission test wavelength in the range 200 to 210 nm, with the grown optical barium fluoride crystal for transmitting below 200 nm wavelengths having an absorption coefficient at 200 to 210 nm<0.0017 cm$^{-1}$. The invention includes a below 200 nm wavelength transmitting optical fluoride crystal of barium fluoride having a below 200 nm transmission greater than 99%/cm and a lead ppb level less than 50 and an absorption coefficient at 200 to 210 nm<0.0017 cm$^{-1}$.

DETAILED DESCRIPTION OF THE PREFERRED EMBODIMENTS

Figure 1A:
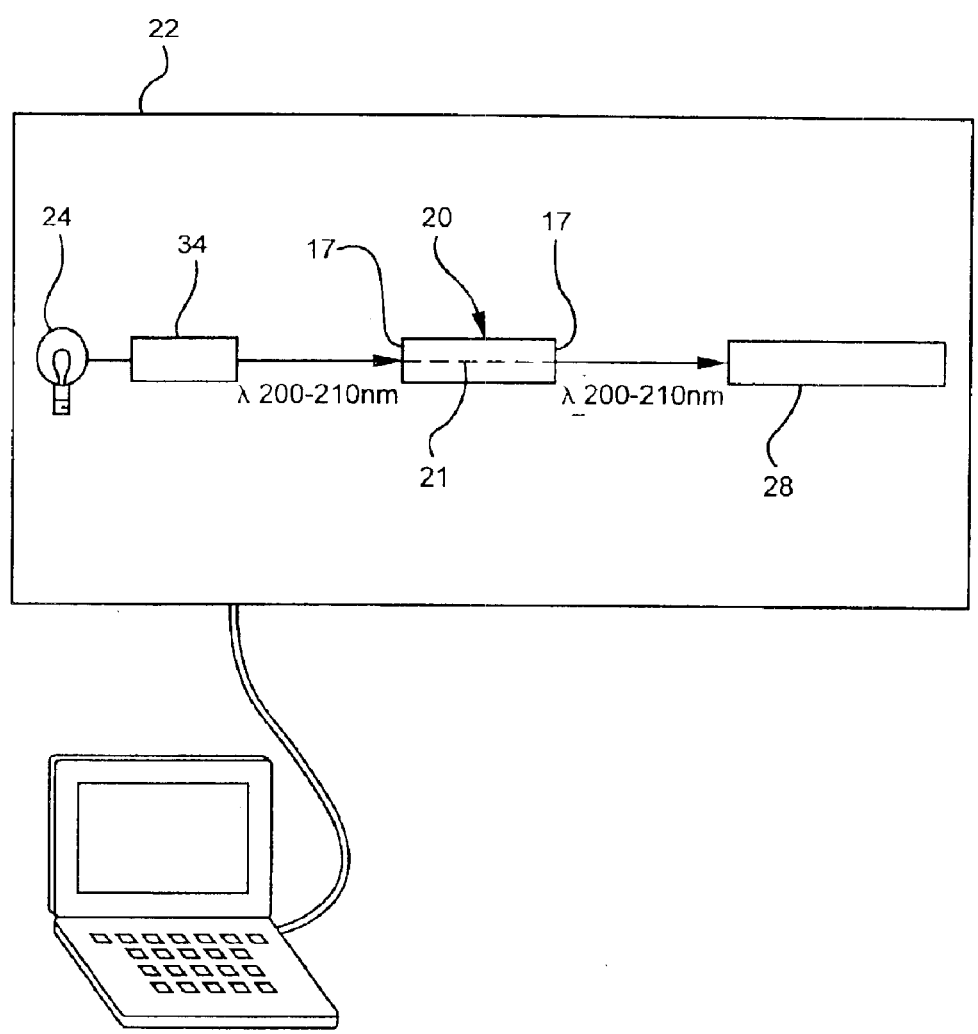
FIGS. 1A–B show an embodiments of the invention.
Figure 1B:
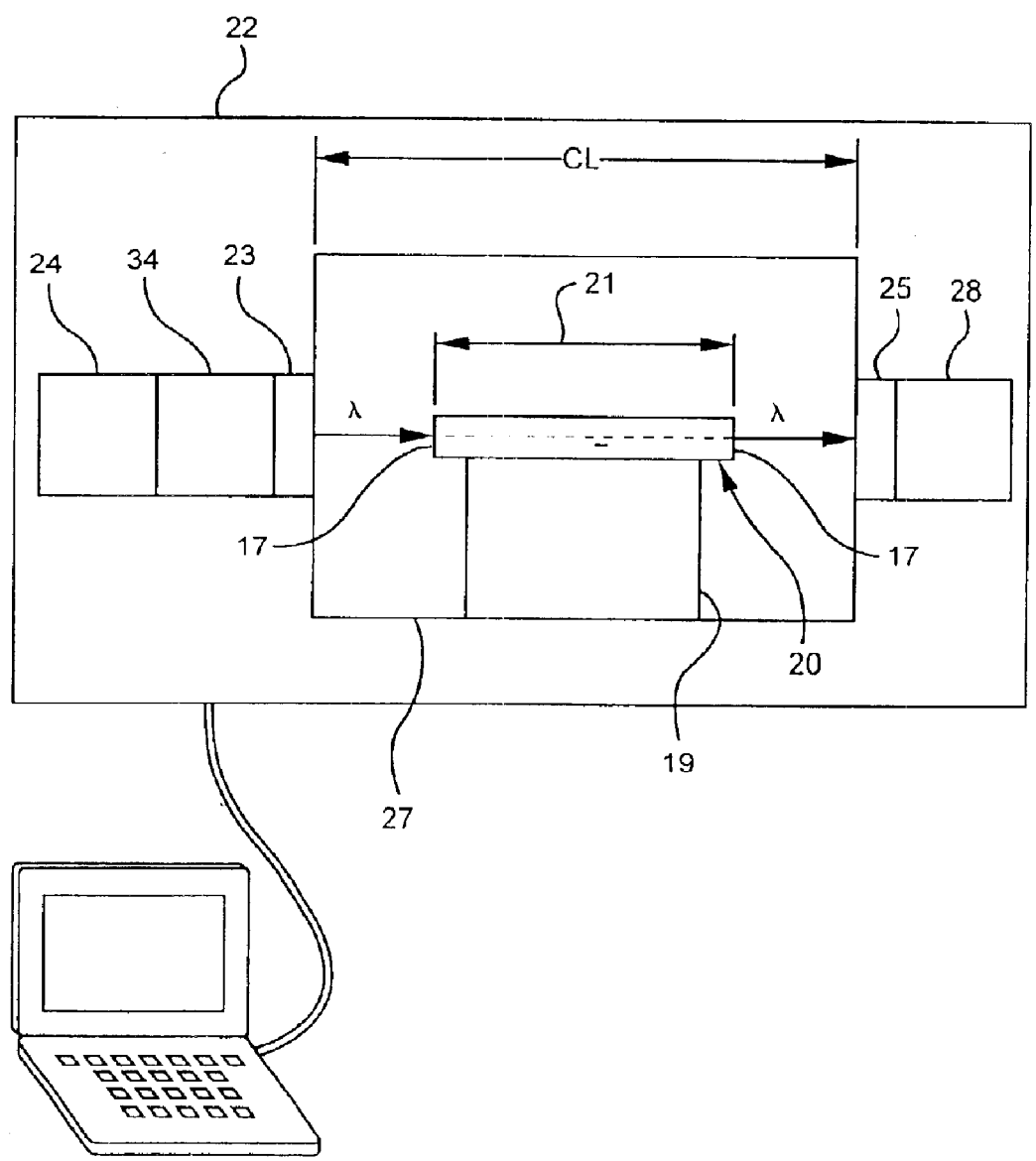

The invention includes a method of detecting sub-ppm lead impurity levels in a below 200 nm transmitting optical fluoride crystal. The method includes providing a below 200 nm wavelength transmitting optical fluoride crystal 20. Optical fluoride crystal 20 preferably is an optical fluoride crystal with a lead contaminant level less than 1 ppm. The method includes providing a light absorption band measurement system spectrometer 22 having a light source 24 for producing a transmission test wavelength in the range 200 to 210 nm and a transmission detector 28 for measuring transmission of the test wavelength. The method includes measuring a lead contaminant level in a path length 21 of the fluoride crystal with the transmission test wavelength in the range 200 to 210 nm. The method includes transmitting the 200–210 nm test wavelength through the below 200 nm wavelength optical fluoride crystal 20 and measuring the transmission of the test wavelength through the crystal to provide a lead ppb impurity level measurement less than 900 ppb, preferably less than 500 ppb, preferably less than 300 ppb, preferably less than 100 ppb, preferably less than 50 ppb, preferably less than 20 ppb, more preferably less than 10 ppb. Preferably light source 24 is a broad band wavelength light source such as a lamp. Preferably light source 24 provides a scannable wavelength spectrum from 200–210 nm. Preferably lamp 24 is a broad band noncoherent light source compared to a laser light source. Providing a 200 to 210 nm test wavelength preferably includes utilizing a wavelength selector 34 such as a monochromator/filter to controllably scan through and select the test wavelengths in the 200–210 range. In a preferred embodiment the scannable wavelength spectrum from 200–210 nm is provided by a deuterium lamp light source controllably filtered with a monochromator. Preferably the spectrophotometer is used to scan the 200–210 nm spectrum. Preferably the method includes using the spectrophotometer to scan the spectrum in the range of centered about 205 nm to identify the pedestal on which the 205 nm absorption band is standing. Then from the total absorption subtract the absorption of the pedestal at 205 nm and thus obtain the lead contaminant level absorption. The scanning of wavelengths centered about 205 nm is preferred to provide a baseline absorption for the crystal so that other background absorption bands together with surface optical losses (pedestal) can be subtracted. In a preferred embodiment for detecting very low levels of lead contamination the scanning of wavelengths centered about 205 nm utilizes a scanning range of about 195–220 nm to identify the pedestal magnitude at 205 nm. The method provides for real time determination of lead impurity levels through the crystal. Transmitting the 200 to 210 nm transmission test wavelength preferably includes transmitting a 203 to 207 nm transmission test wavelength in the range 203 to 207 nm through the below 200 nm wavelength transmitting optical fluoride crystal light transmission path length and measuring the transmission of the 203 to 207 nm test wavelength through the path length to provide a lead ppb impurity level measurement less than 500 ppb. Preferably transmitting the 200 to 210 nm transmission test wavelength comprises transmitting an about 205 nm transmission test wavelength through the below 200 nm wavelength transmitting optical fluoride crystal light transmission path length and measuring the transmission of said the 205 nm test wavelength through the path length to provide a lead ppb impurity level measurement less than 300 ppb. In a preferred embodiment of the invention providing a below 200 nm wavelength transmitting optical fluoride crystal having a crystal light transmission path length $\geq 2$ mm comprises providing a crystal light transmission path length $\geq 1$ cm and transmitting the transmission test wavelength through the $\geq 1$ cm fluoride crystal light transmission path length to provide a lead ppb impurity level measurement less than 100 ppb. More preferably the crystal light transmission path length is $\geq 10$ cm and transmitting the transmission test wavelength through the $\geq 10$ cm fluoride crystal light transmission path length provides a lead ppb impurity level measurement less than 50, more preferably less than 10 ppb. As shown in FIGS. 1A–B, the fluoride crystal light transmission path length for the spectrophotometer measurement is designated 21. As shown in FIG. 1B, the spectrophotometer 22 has a chamber 27 that has a length CL between the chamber beam windows 23 and 25, preferably with 0.5 CL$\geq$fluoride crystal light transmission path length. Preferably the spectrophotometer includes a chamber sample holder 19 to hold and stabilize crystal sample 20 relative to windows 23 and 25. Chamber sample holder 19 receives the long crystal sample and ensures alignment with the transmission test wavelength light beam in the chamber between the windows with the crystal sample centrally located in the middle of the chamber. Preferably crystal 20 has polished faces 17. Preferably the path length 21 is at least 50 mm (50–100 mm) to provide preferred lead concentration measurements in the few ppb range (lead <10 ppb) with the parallelism of faces 17 better than 1 degree. For lead concentration measurements in the few tens ppb range (10 ppb<lead<100 ppb) the path length 21 is the range of 5–10 mm. Preferably the fluoride crystal sample path length is at least 50 mm, more preferably at least 90 mm (100 mm preferred embodiment) with the spectrophotometer chamber length between windows CL at least 100 mm, more preferably CL$\geq$150 mm, most preferably CL$\geq$200 mm (200 mm preferred embodiment).

The invention includes a method of measuring below 1 ppm impurity levels in an optical fluoride lithography crystal for transmitting below 200 nm wavelength light, such as a calcium or barium fluoride crystal 20. The method includes providing a below 200 nm wavelength transmitting optical fluoride crystal 20 having a crystal light transmission path length 21 that is $\geq 1$ cm and providing a 200–210 nm absorption measurement system spectrophotometer 22 having a light source 24 for producing a test wavelength in the range 200 to 210 nm and a transmission detector for calculating an absorption coefficient at the test wavelength. The method includes transmitting the 200 to 210 nm range test wavelength through the below 200 nm wavelength transmitting optical fluoride crystal light transmission $\geq 1$ cm path length and measuring the absorption coefficient at the test wavelength through the $\geq 1$ cm path length to provide a lead contaminant level absorption coefficient <0.0017 cm$^{-1}$. Preferably the method includes transmitting a 203 to 207 nm test wavelength in the range 203 to 207 nm through the below 200 nm wavelength transmitting optical fluoride crystal light transmission $\geq 1$ cm path length and measuring the absorption coefficient at the 203 to 207 nm test wavelength through said $\geq 1$ cm path length to provide a lead contaminant level absorption coefficient <0.0016 cm$^{-1}$. More preferably the includes transmitting an about 205 nm test wavelength through the below 200 nm wavelength transmitting optical fluoride crystal light transmission $\geq 1$ cm path length and measuring the absorption coefficient at the 205 nm test wavelength through said $\geq 1$ cm path length to provide a lead contaminant level absorption coefficient <0.0015 cm$^{-1}$. Providing a below 200 nm wavelength transmitting optical fluoride crystal 20 having a crystal light transmission path length 21 comprises providing a crystal light transmission path length $\geq 10$ cm to provide a lead contaminant level absorption coefficient impurity measurement less than 50 ppb, preferably $\leq 20$, preferably $\leq 10$, preferably $\leq 5$, and most preferably $\leq$about 1 ppb.

Figure 2:
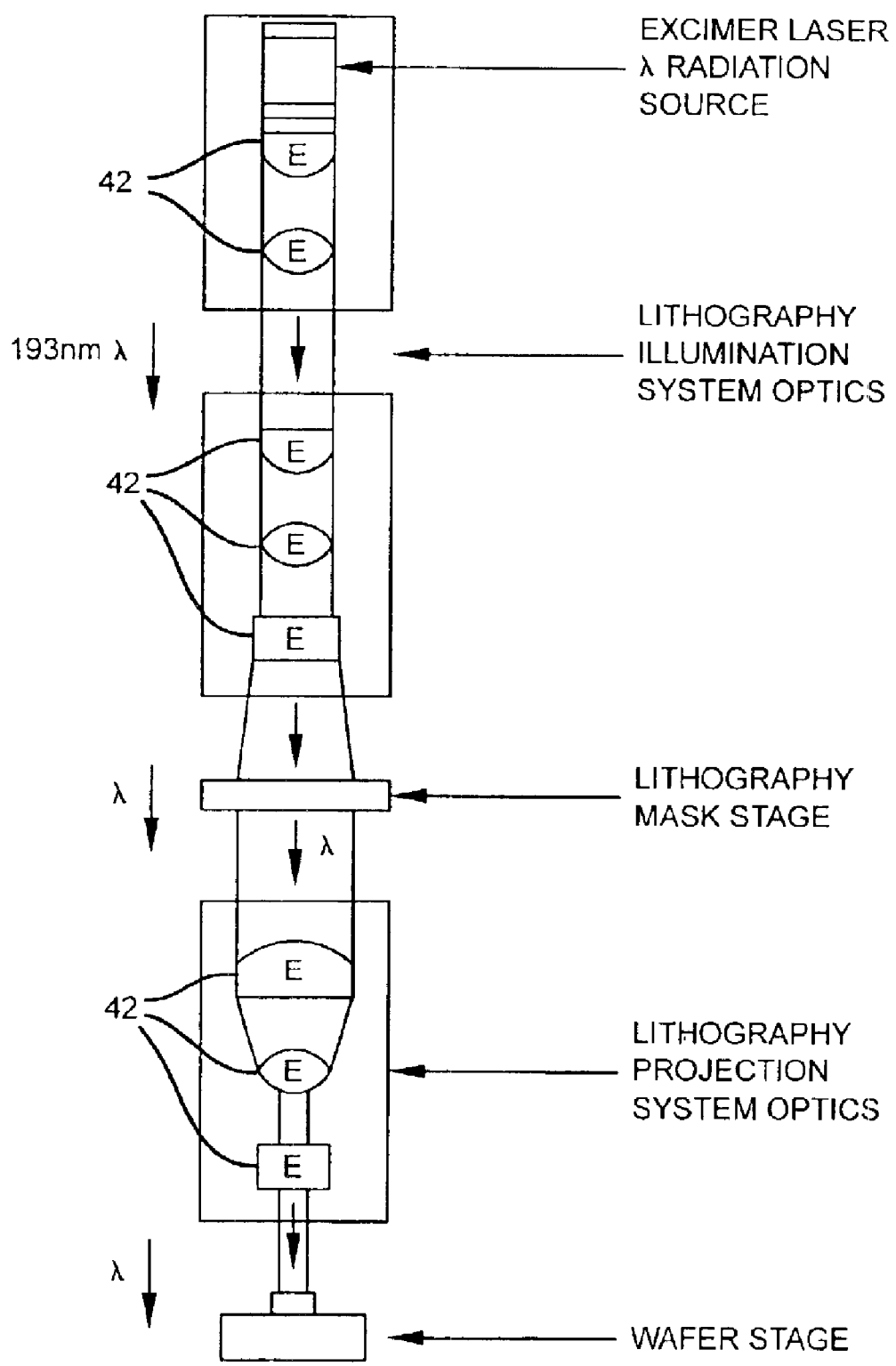
FIG. 2 shows an embodiment of the invention.
Figure 3:
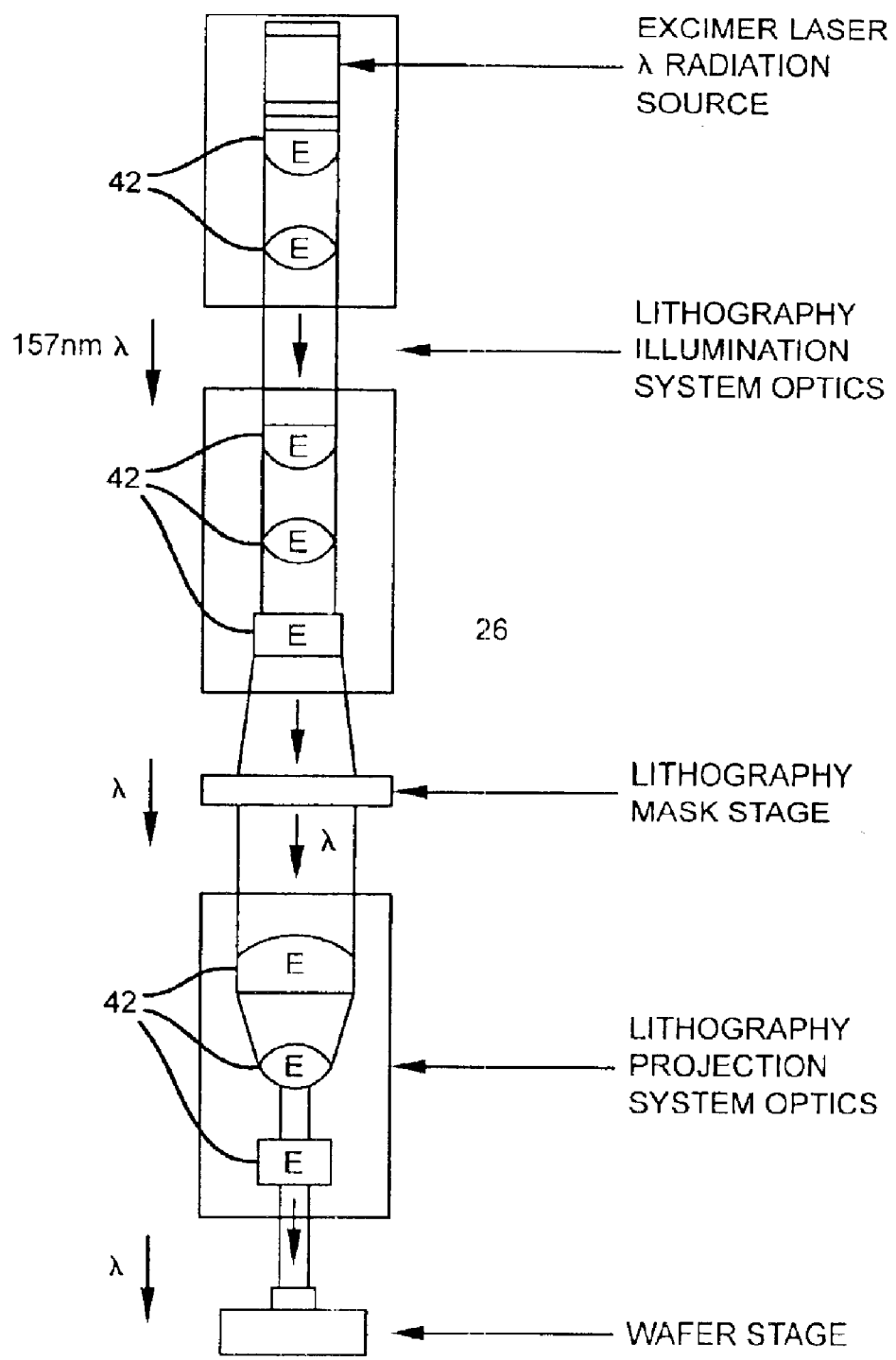
FIG. 3 shows an embodiment of the invention.
Figure 4:
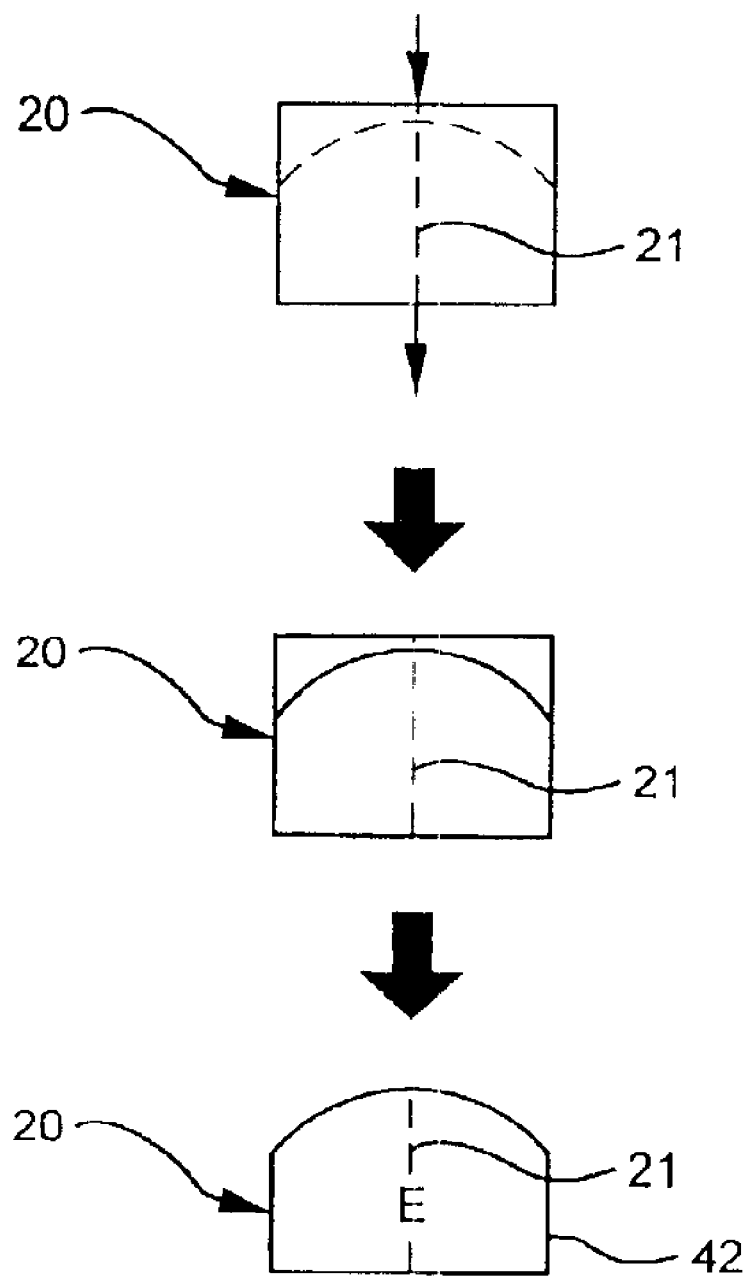
FIG. 4 shows an embodiment of the invention.

The invention includes a method of making a below 200 nm wavelength optical element E for transmitting below 200 nm wavelength light such as $F_2$ excimer laser 157 nm output or an ArF excimer laser 193 nm output as shown in FIGS. 2–3. Preferably the method includes making a $\lambda<200$ nm optical lithography element 42 of high optical quality from an optical fluoride crystal 20 having a lead contaminant level measurement less than 100 ppb. The method includes providing a below 200 nm wavelength transmitting optical fluoride crystal 20 having a crystal light transmission path length 21 that is $\geq 2$ mm and providing a light transmission 200–210 nm photometer spectrophotometer 22 having a light source 24 for producing a transmission test wavelength in the range 200 to 210 nm and a transmission detector 28 for measuring transmission of said test wavelength. The method includes transmitting the transmission test wavelengths (200 to 210 nm) through the below 200 nm wavelength transmitting optical fluoride crystal light transmission path length and measuring the transmission of the 200 to 210 nm test wavelengths through the path length to provide a lead contaminant level measurement less than 500 ppb , preferably <100 ppb and forming the optical fluoride crystal into a below 200 nm wavelength optical element E having a lead contaminant absorption coefficient at 200 to 210 nm<0.0017 cm$^{-1}$. Preferably the contaminant level measurement is less than 100 ppb, more preferably <50 ppb, more preferably <20 ppb, and most preferred less than 10 ppb. Providing a below 200 nm wavelength transmitting optical fluoride crystal 20 having a crystal light transmission path length 21 comprises providing a below 200 nm wavelength transmitting optical fluoride crystal 20 having a crystal light transmission path length $\geq 1$ cm and transmitting a 203 to 207 nm test wavelength in the range 203 to 207 nm through the below 200 nm wavelength transmitting optical fluoride crystal light transmission $\geq 1$ cm path length 21 and measuring the absorption coefficient at said 203 to 207 nm test wavelength through the path length to provide a lead contaminant level measurement less than 50 ppb and forming the optical fluoride crystal into a below 200 nm wavelength optical element E having an absorption coefficient at 203 to 207 nm<0.0016 cm$^{-1}$. Preferably the crystal light transmission path length is $\geq 10$ cm and the method includes transmitting an about 205 nm test wavelength through the below 200 nm wavelength transmitting optical fluoride crystal light transmission $\geq 10$ cm path length and measuring the absorption coefficient at about 205 nm through the $\geq 10$ cm path length to provide a lead contaminant level measurement less than 20 ppb and forming the optical fluoride crystal into a below 200 nm wavelength optical element E having an absorption coefficient at 205 nm<0.0016 cm$^{-1}$. In a preferred embodiment the below 200 nm wavelength transmitting optical fluoride crystal 20 is comprised of calcium fluoride, preferably CaF$_2$. In a preferred embodiment the below 200 nm wavelength transmitting optical fluoride crystal 20 is comprised of barium fluoride, preferably BaF$_2$. In a preferred embodiment, such as shown in FIG. 4, the 200 to 210 nm test wavelength through the path length 21 of crystal 20 is utilized in manufacturing to measure the lead contaminant level in the crystal so that the end product below 200 nm optical element E (formed from the crystal) has an absorption coefficient at 200 to 210 nm<0.0017 cm$^{-1}$. Preferably crystal 20 and optical element 42 formed therefrom have a measured contaminant lead level less than 20 ppb, more preferably <10 ppb, more preferably <1 ppb. Providing below 200 nm transmitting optical fluoride crystal 20 preferably includes providing a calcium fluoride crystal with a λ<200 nm transmission greater than 99%/cm. The method provides an optical lithography element 42 with a measured contaminant level less than 50 ppb, and if optical coatings are to be applied to the crystal surface, preferably measured prior to any such coating. Providing below 200 nm transmitting optical fluoride crystal 20 alternatively preferred includes providing a barium fluoride crystal with a λ<200 nm transmission greater than 99%/cm. The method provides an optical lithography element 42 with a measured contaminant level less than 50 ppb and an absorption coefficient at 200 to 210 nm<0.0017 cm$^{-1}$, and if optical coatings are to be applied to the crystal surface, preferably measured prior to any such coating.

Figure 5:
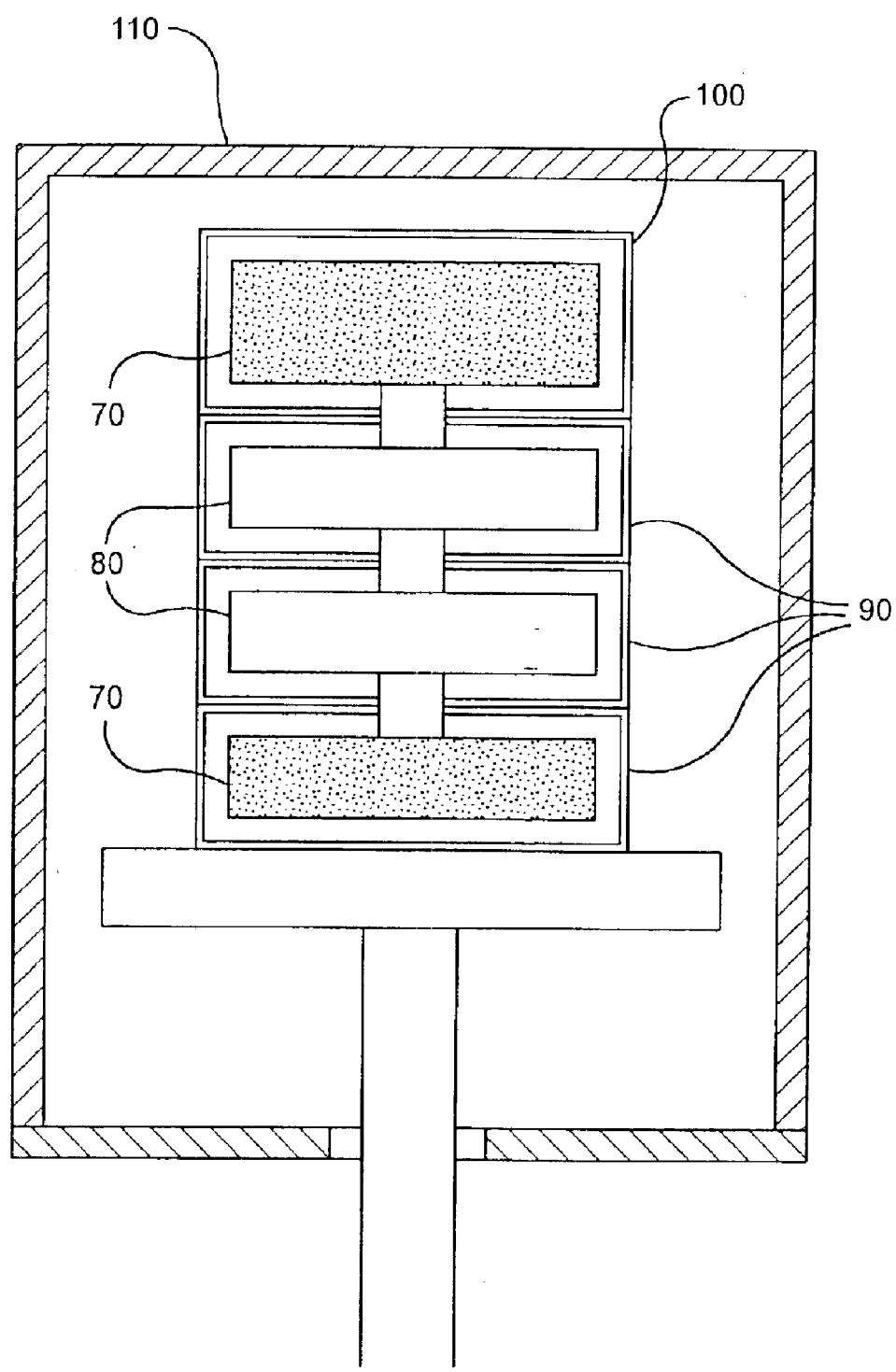
FIG. 5 shows an embodiment of the invention.
Figure 7:
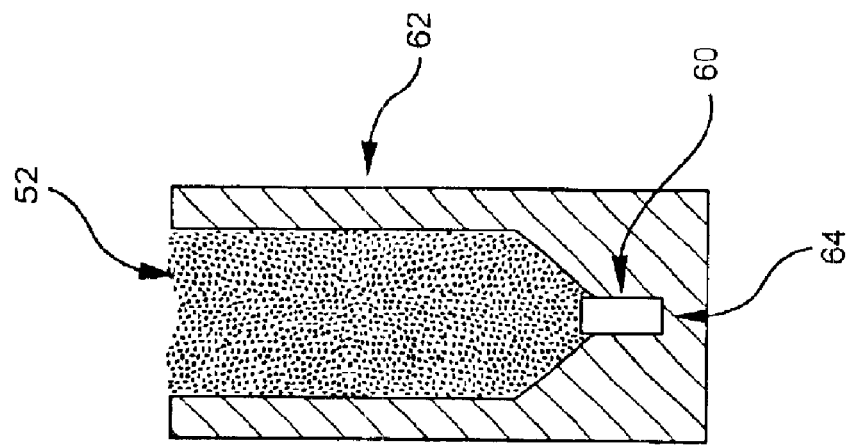
FIG. 7 shows an embodiment of the invention.
Figure 6:
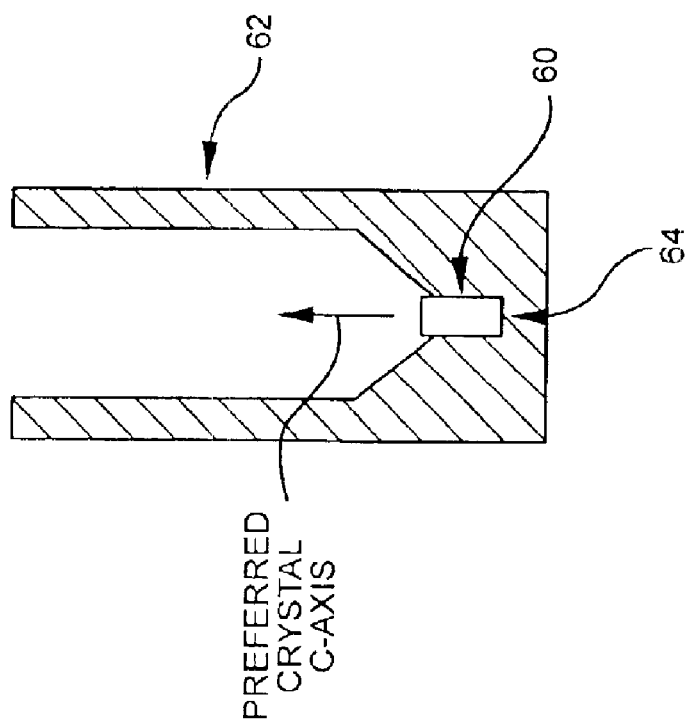
FIG. 6 shows an embodiment of the invention.
Figure 8:
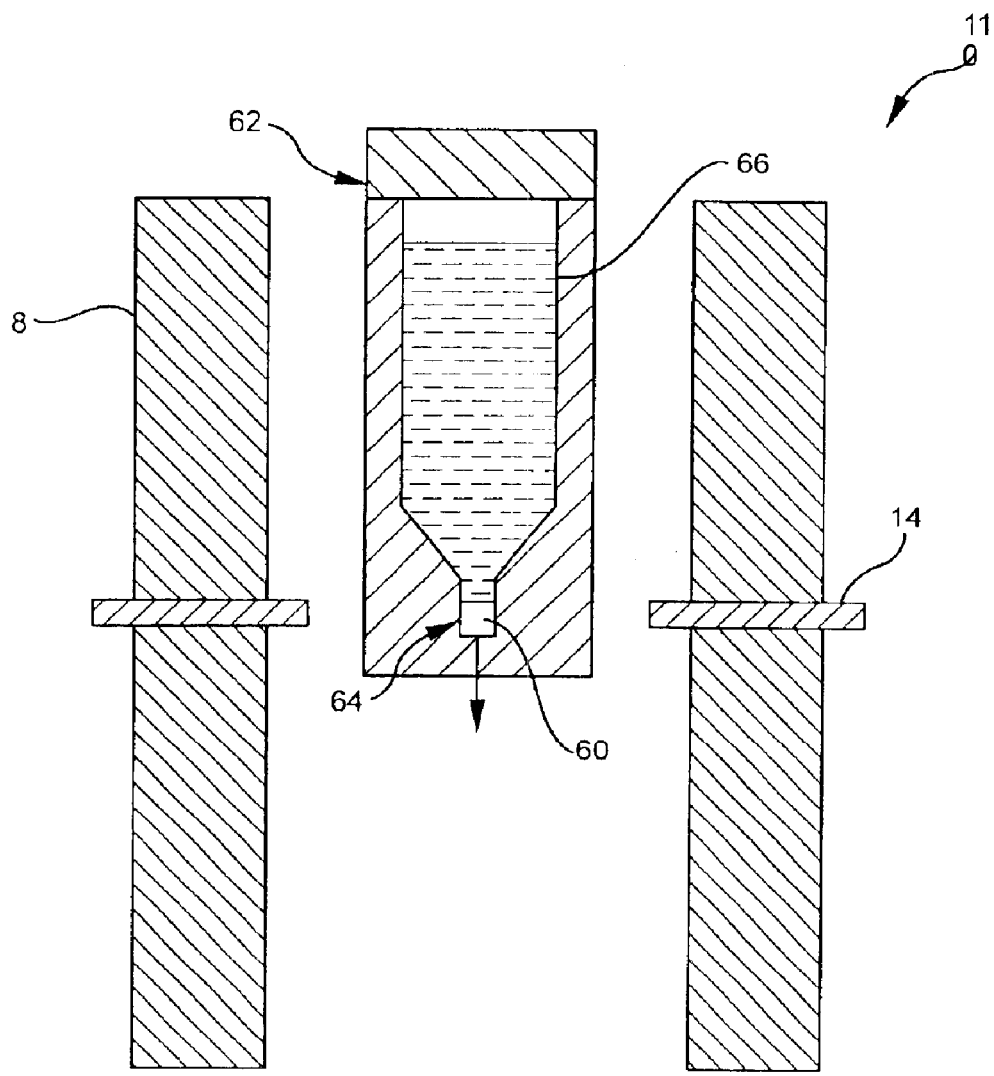
FIG. 8 shows an embodiment of the invention.
Figure 9:
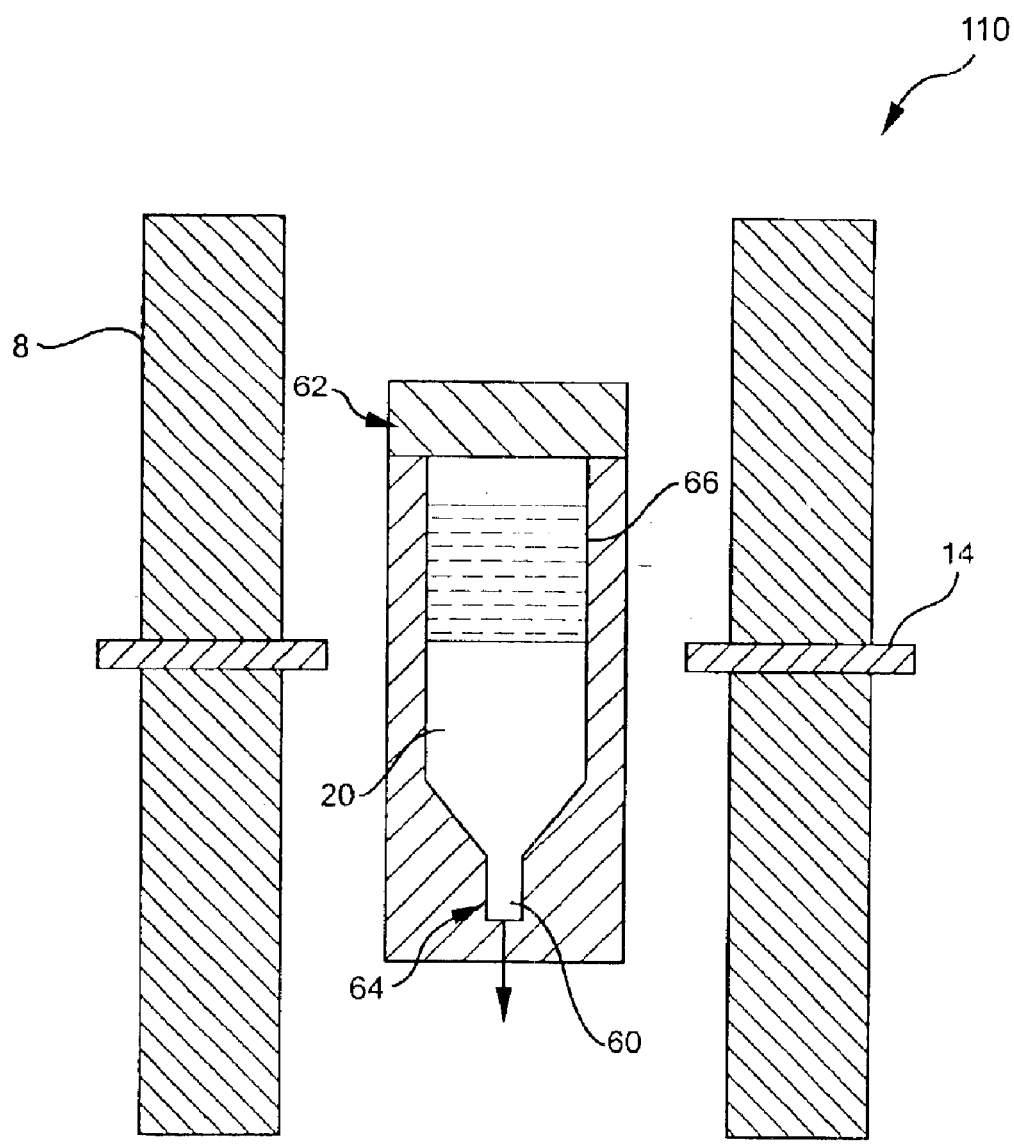
FIG. 9 shows an embodiment of the invention.
Figure 10:
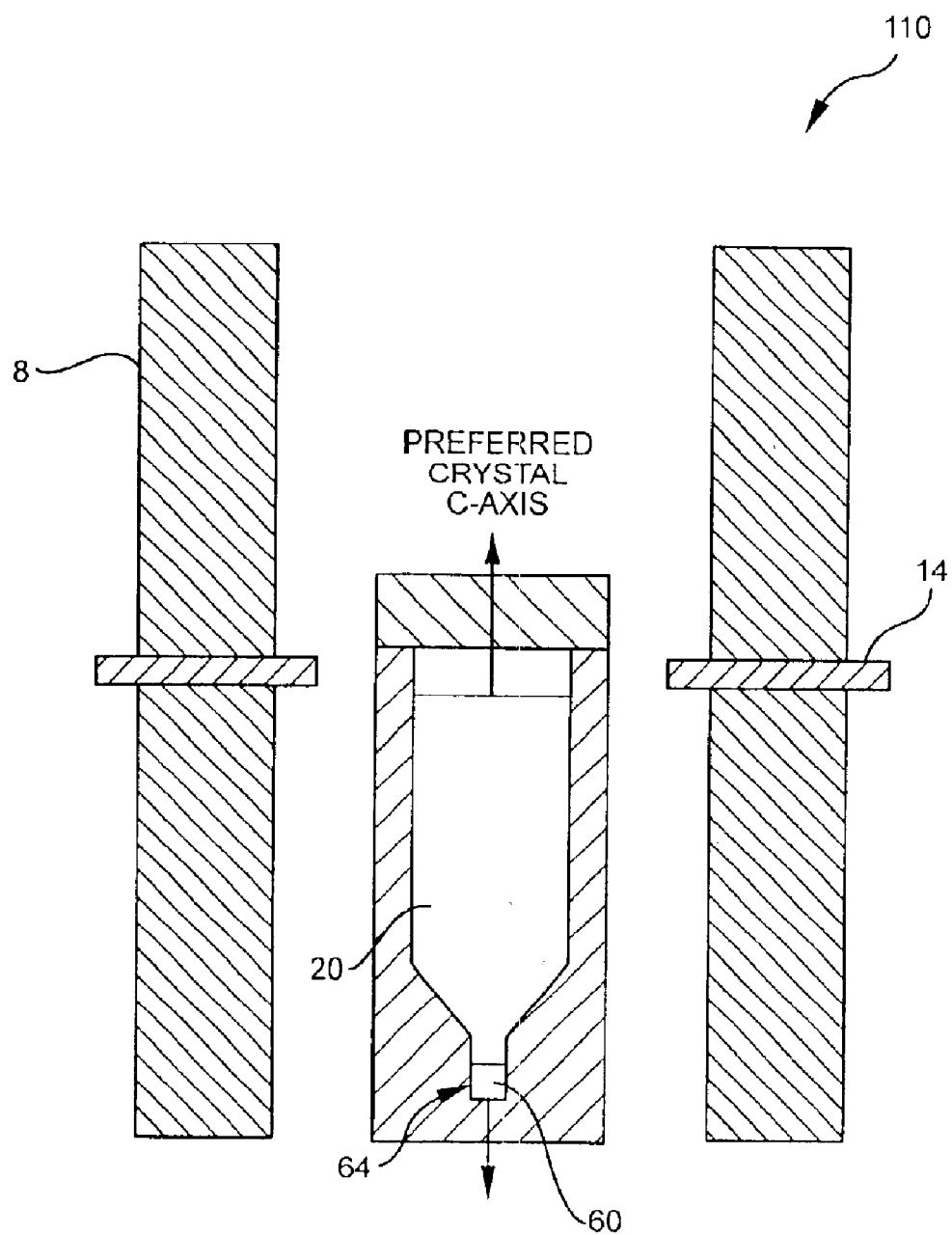
FIG. 10 shows an embodiment of the invention.
Figure 11:
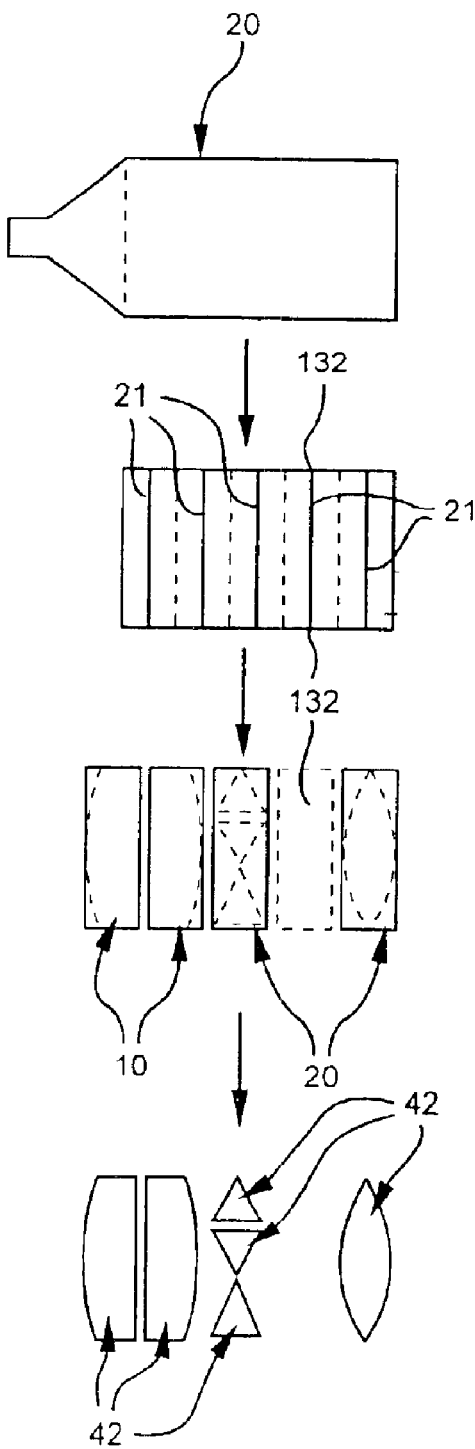
FIG. 11 shows an embodiment of the invention.
Figure 12:
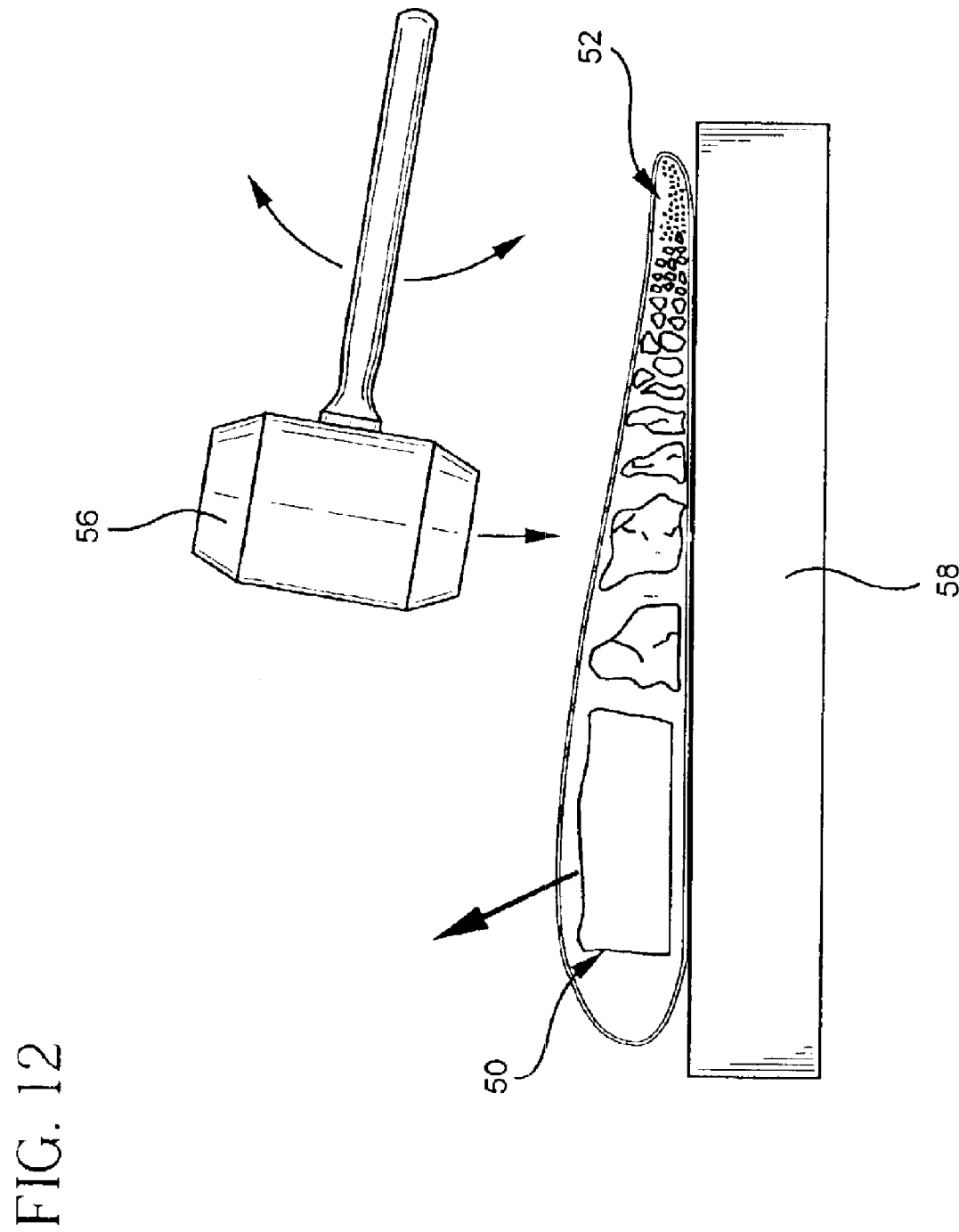
FIG. 12 shows an embodiment of the invention.
Figure 13A:
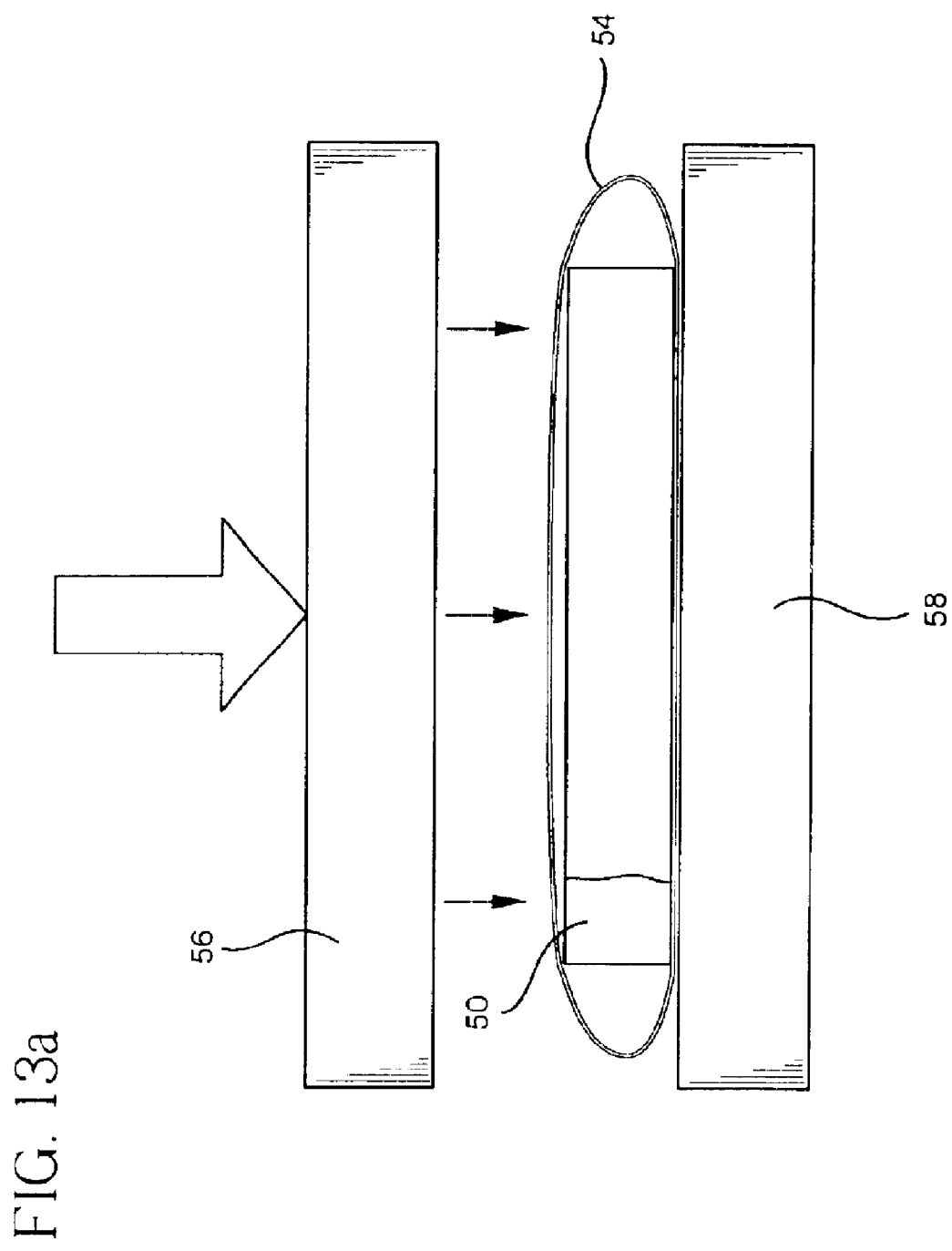
FIGS. 13a–c shows an embodiment of the invention.
Figure 13B:
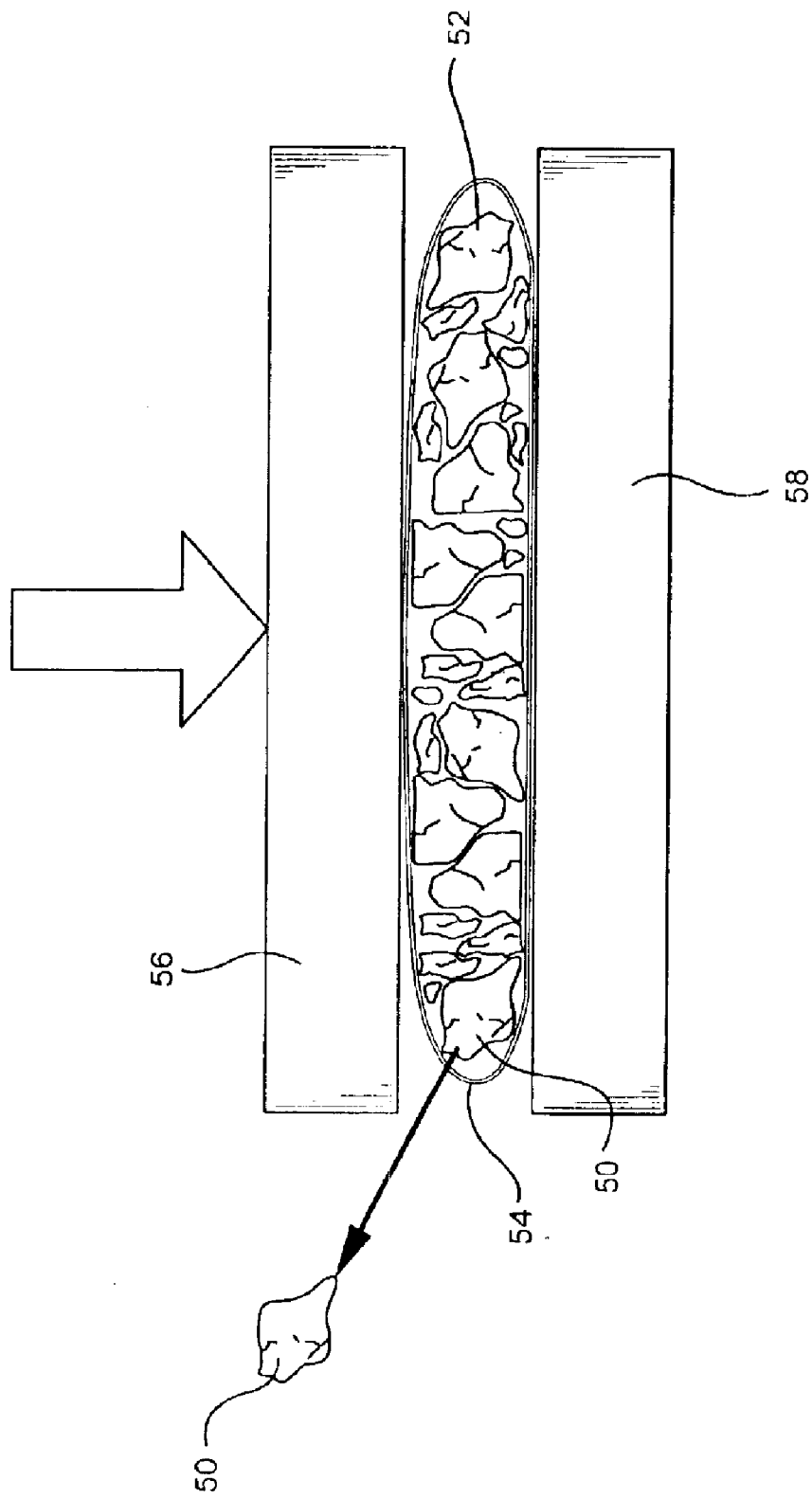
Figure 13C:
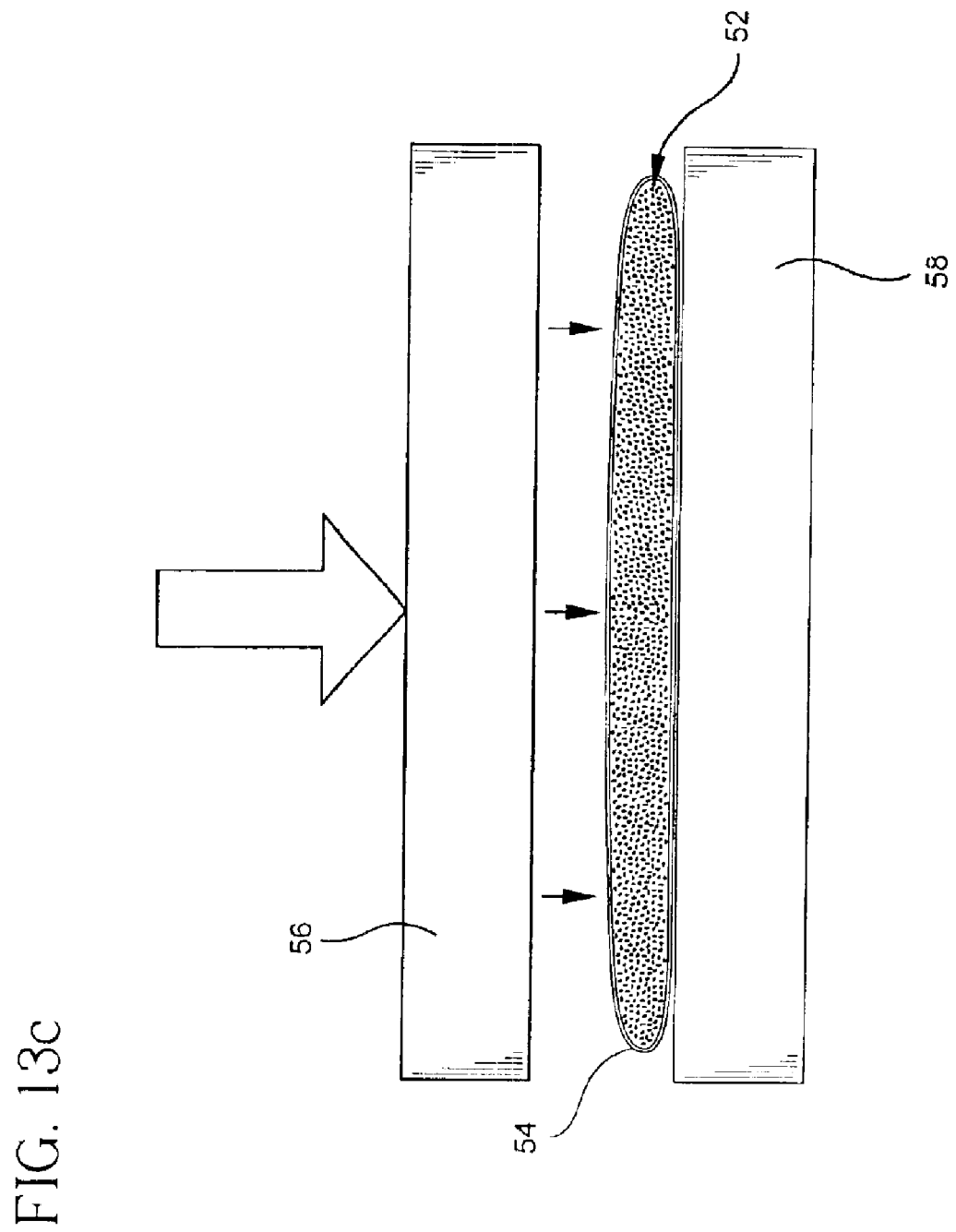

The invention includes a method of making a below 200 nm wavelength transmitting optical fluoride crystal 20. The method includes providing a premelt calcium fluoride crystal solid and melting the calcium fluoride crystal solid to form a calcium fluoride melt and growing a calcium fluoride crystal from the melt to provide an optical calcium fluoride crystal for transmitting below 200 nm wavelengths. The method includes providing a light transmission 200–210 nm photometer spectrophotometer having a light source for producing a transmission test wavelength in the range 200 to 210 nm and a transmission detector for measuring transmission of the test wavelength and measuring a lead contaminant level in a calcium fluoride path length with the transmission test wavelength in the range 200 to 210 nm, with the grown optical calcium fluoride crystal for transmitting below 200 nm wavelengths having an absorption coefficient at 200 to 210 nm<0.0017 cm$^{-1}$. In an embodiment, measuring the lead contaminant level in the calcium fluoride with the 200–210 nm spectrometer includes measuring the lead contaminant level in the premelt calcium fluoride crystal solid. In an embodiment measuring the lead contaminant level in the calcium fluoride with the 200–210 nm spectrophotometer 22 includes measuring the lead contaminant level in the calcium fluoride crystal grown from the calcium fluoride melt. In an embodiment, the lead contaminant level in the calcium fluoride is measured with the 200–210 nm spectrometer when the crystal is in the formed shape of an optical element E before optical coating. In an embodiment, the lead contaminant level in the calcium fluoride is measured prior to crushing into the particulate form and/or during the crushing process of crushing from a large solid block into smaller pieces. Preferably the measuring and monitoring of lead contaminant level in the crystal making process provides a grown optical calcium fluoride crystal for transmitting below 200 nm wavelengths with a lead ppb contaminant excitation level less than 50 ppb, more preferably <20 ppb. Preferably the grown optical fluoride crystal 20 has a lead ppb contaminant level less than 10 ppb, preferably <1 ppb. FIG. 5 shows an embodiment of the invention wherein a vacuum controlled atmosphere crystallization furnace 110 is loaded with stacked interconnected graphite crucibles 90 and top reservoir crucible 100. The middle crucibles are loaded with premelt calcium fluoride crystal solid dense discs 80. Premelt calcium fluoride crystal solid discs 80 are purified and densified CaF$_2$ preferably obtained from a premelt process wherein high purity raw material is purified and densified by heating and melting with a fluorinating agent. In an embodiment the premelt calcium fluoride crystal solid is obtained by premelt purification and densification utilizing PbF$_2$ as a fluorinating agent with the calcium fluoride, with the controlled atmosphere vacuum furnace operated to remove volatile lead and oxygen products from the crystal material. In an embodiment, such as shown in FIG. 5, the furnace can also be loaded with calcium fluoride powder particulate 70 which can include a fluorinating agent such as lead fluoride. The premelt calcium fluoride crystal solid loaded into crystal growth furnace 110 is melted in the crucibles into a calcium fluoride melt which is then grown into a calcium fluoride crystal 20 by slowly cooling the melt within the crystal growth furnace, such as lowering through the thermal gradient in a Stockbarger crystal growth process. In another embodiment of the invention shown in FIGS. 6–10, a growth crucible 62 having a preferred crystal axis oriented seed crystal 60 in a seed crystal receiver 64 is utilized. Premelt calcium fluoride crystal solid particulate 52 is loaded into crucible 62. The crystal growth crucible containing the premelt calcium fluoride crystal solid is loaded into an optical fluoride growth furnace 110, which includes a high temperature upper melt zone 8 and a thermal baffle 14 which provides a thermal gradient for crystal growth solidification. The calcium fluoride crystal solid loaded into crucible 62 is melted in the high temperature zone 8 of furnace 100 to form a calcium fluoride melt 66. Calcium fluoride optical crystal 20 is grown from the melt 66 by lowering through the crystal growth solidification zone of baffle 14 to provide optical fluoride crystal 20 for transmitting below 200 nm wavelengths. The method includes making the crystal 20 by utilizing a 200–210 nm transmission photometer 22 to measure lead contaminant levels in calcium fluoride such as in the premelt calcium fluoride crystal solids 80, in the grown crystal 20, and the seed 60. The 200–210 nm spectrometer 22 is preferably utilized throughout the crystal manufacturing process to measure, monitor, and control the calcium fluoride lead content, particularly when lead fluoride is used as a fluorinating agent, which needs to be removed from the end product crystal 20 and optical element E thereof to provide high transmission and optical properties at below 200 nm wavelengths. The 200–210 nm spectrometer calcium fluoride lead contaminant level measurements are utilized to provide measurements below 50 ppb, preferably below 20, preferably below 10 ppb, more preferably below 1 ppb by weight. The 200–210 nm spectrometer calcium fluoride lead contaminant level measurements can be utilized to identify high lead contaminant level areas of crystals and remove them from the optical fluoride crystal optical element making process as rejects. Such as shown in FIG. 11, the lead contaminant measurements can be utilized to identify a high contaminant local crystal region area 132 with an absorption coefficient at 200 to 210 nm>0.0017 cm$^{-1}$, and remove such high lead contaminant region area 132 from further processing into separate optical element blank preform crystals 20 and into optical elements 42 made therefrom. Such as shown in FIGS. 12–13C the measurements can be utilized to identify a high lead contaminant local crystal area 50 in premelt solid 52 to provide a high purity premelt solid particulate resulting from a crushing process using crushers 56 and 58. The high contaminant areas 50 can be identified with the 200–210 nm transmission spectrophotometer as having an absorption coefficient at 200 to 210 nm>0.0017 cm$^{-1}$ and be removed during the crushing process from the low lead contaminant areas to result in the production of a separated low lead impurity premelt solid 52. Preferably the 200–210 nm transmission measurements are utilized to provide a calcium fluoride with less than 100 ppb lead, preferably less than 50 ppb lead, to result in a grown calcium fluoride crystal and optical element formed therefrom that have an absorption coefficient at 200 to 210 nm<0.0017 cm$^{-1}$, preferably an absorption coefficient at 203 to 207 nm<0.0017 cm$^{-1}$, more preferably an absorption coefficient at 205 nm<0.0017 cm$^{-1}$. Such a method of making optical fluoride crystals and optical elements therefrom while monitoring and measuring lead impurity level, utilizing a 200–210 nm spectrophotometer at 200 to 210 nm provides for a high quality crystal with excellent optical properties including high below 200 nm transmission greater than 99%/cm, most preferably 157 nm transmission greater than 99%/cm. The method of making optical fluoride crystals produces fluoride crystals with a lead level less than 50 ppb, more preferably <20 ppb, more preferably <10 ppb, more preferably <1 ppb and most preferably below 200 nm wavelength transmitting calcium fluoride elements with a lead ppb excitation level less than 1 ppb by weight. The invention includes a below 200 nm wavelength transmitting optical fluoride crystal. The optical fluoride crystal 20 is comprised of calcium fluoride having a below 200 nm transmission greater than 99%/cm, preferably 157 nm transmission >99%/cm, and a lead ppb level less than 50 and an absorption coefficient at 200 to 210 nm<0.0017 cm$^{-1}$, more preferably a 203 to 207 nm absorption coefficient <0.0017 cm$^{-1}$, and most preferably a 205 nm absorption coefficient <0.0016 cm$^{-1}$. Preferably the lead ppb level is less than 10, more preferably <1 by weight. The lead analysis method of the invention can be utilized throughout the optical fluoride crystal optical element manufacturing process to the end product optical element.

The invention includes a method of making a below 200 nm wavelength transmitting optical fluoride crystal 20. The method includes providing a premelt barium fluoride crystal solid and melting the barium fluoride crystal solid to form a barium fluoride melt and growing a barium fluoride crystal from the melt to provide an optical barium fluoride crystal for transmitting below 200 nm wavelengths. The method includes providing a light transmission 200–210 nm spectrophotometer having a light source for producing a transmission test wavelength in the range 200 to 210 nm and a transmission detector for measuring transmission of the test wavelength and measuring a lead contaminant level in a barium fluoride path length with the transmission test wavelength in the range 200 to 210 nm, with the grown optical barium fluoride crystal for transmitting below 200 nm wavelengths having a an absorption coefficient at 200 to 210 nm<0.0017 cm$^{-1}$. In an embodiment, measuring the lead contaminant level in the barium fluoride with the 200–210 nm spectrometer includes measuring the lead contaminant level in the premelt barium fluoride crystal solid. In an embodiment measuring the lead contaminant level in the barium fluoride with the 200–210 nm spectrophotometer 22 includes measuring the lead contaminant level in the barium fluoride crystal grown from the barium fluoride melt. In an embodiment, the lead contaminant level in the barium fluoride is measured with the 200–210 nm spectrometer when the crystal is in the formed shape of an optical element E before optical coating. In an embodiment, the lead contaminant level in the barium fluoride is measured prior to crushing into the particulate form and/or during the crushing process of crushing from a large solid block into smaller pieces. Preferably the measuring and monitoring of lead contaminant level in the crystal making process provides a grown optical barium fluoride crystal for transmitting below 200 nm wavelengths with a lead ppb contaminant level less than 50 ppb, more preferably <20 ppb. Preferably the grown optical fluoride crystal 20 has a lead ppb contaminant level less than 10 ppb, preferably <1 ppb. FIG. 5 shows an embodiment of the invention wherein a vacuum controlled atmosphere crystallization furnace 110 is loaded with stacked interconnected graphite crucibles 90 and top reservoir crucible 100. The middle crucibles are loaded with premelt barium fluoride crystal solid dense discs 80. Premelt barium fluoride crystal solid discs 80 are purified and densified BaF$_2$ preferably obtained from a premelt process wherein high purity raw material is purified and densified by heating and melting with a fluorinating agent. In an embodiment the premelt barium fluoride crystal solid is obtained by premelt purification and densification utilizing PbF$_2$ as a fluorinating agent with the barium fluoride, with the controlled atmosphere vacuum furnace operated to remove volatile lead and oxygen products from the crystal material. In an embodiment, such as shown in FIG. 5, the furnace can also be loaded with barium fluoride powder particulate 70 which can include a fluorinating agent such as lead fluoride. The premelt barium fluoride crystal solid loaded into crystal growth furnace 110 is melted in the crucibles 90 and 100 into a barium fluoride melt which is then grown into a barium fluoride crystal 20 by slowly cooling the melt within the crystal growth furnace, such as lowering through the thermal gradient in a Stockbarger crystal growth process. In another embodiment of the invention shown in FIGS. 6–10, a growth crucible 62 having a preferred crystal axis oriented seed crystal 60 in a seed crystal receiver 64 is utilized. Premelt barium fluoride crystal solid particulate 52 is loaded into crucible 62. The crystal growth crucible containing the premelt barium fluoride crystal solid is loaded into an optical fluoride growth furnace 110, which includes a high temperature upper melt zone 8 and a thermal baffle 14 which provides a thermal gradient for crystal growth solidification. The barium fluoride crystal solid loaded into crucible 62 is melted in the high temperature zone 8 of furnace 100 to form a barium fluoride melt 66. Barium fluoride optical crystal 20 is grown from the melt 66 by lowering through the crystal growth solidification zone of baffle 14 to provide optical fluoride crystal 20 for transmitting below 200 nm wavelengths. The method includes making the crystal 20 by utilizing a light transmission 200–210 nm photometer 22 to measure lead contaminant levels in barium fluoride such as in the premelt barium fluoride crystal solids 80, in the grown crystal 20, and the seed 60. The 200–210 nm spectrophotometer 22 is preferably utilized throughout the crystal manufacturing process to measure, monitor, and control the barium fluoride lead content, particularly when lead fluoride is used as a fluorinating agent, which needs to be removed from the end product crystal 20 and optical element E thereof to provide high transmission and optical properties at below 200 nm wavelengths. The 200–210 nm spectrometer barium fluoride lead contaminant level measurements are utilized to provide measurements below 50 ppb, preferably below 20, preferably below 10 ppb, more preferably below 1 ppb by weight. The 200–210 nm spectrophotometer barium fluoride lead contaminant level measurements can be utilized to identify high lead contaminant level areas of crystals and remove them from the optical fluoride crystal optical element making process as rejects. Such as shown in FIG. 11, the lead contaminant measurements can be utilized to identify a high contaminant local crystal region area 132 with an absorption coefficient at 200 to 210 nm>0.0017 cm$^{-1}$, and remove such high lead contaminant region area 132 from further processing into separate optical element blank preform crystals 20 and into optical elements 42 made therefrom. Such as shown in FIGS. 12–13C the measurements can be utilized to identify a high lead contaminant local crystal area 50 in premelt solid 52 to provide a high purity premelt solid particulate resulting from a crushing process using crushers 56 and 58. The high contaminant areas 50 can be identified with the 200–210 nm spectrometer as having an absorption coefficient at 200 to 210 nm>0.0017 cm$^{-1}$ and be removed during the crushing process from the low lead contaminant areas to result in the production of a separated low lead impurity premelt solid 52. Preferably the 200–210 nm spectrophotometer measurements are utilized to provide a barium fluoride with less than 100 ppb lead, preferably less than 50 ppb lead, to result in a grown barium fluoride crystal and optical element formed therefrom that have an absorption coefficient at 200 to 210 nm<0.0017 cm$^{-1}$, preferably an absorption coefficient at 203 to 207 nm<0.0017 cm$^{-1}$, more preferably an absorption coefficient at 205 nm<0.0017 cm$^{-1}$. Such a method of making optical fluoride crystals and optical elements therefrom while monitoring and measuring lead impurity level, utilizing a 200–210 nm spectrometer at 200 to 210 nm provides for a high quality crystal with excellent optical properties including high below 200 nm transmission greater than 99%/cm, most preferably 157 nm transmission greater than 99%/cm. The method of making optical fluoride crystals produces fluoride crystals with a lead level less than 50 ppb, more preferably <20 ppb, more preferably <10 ppb, more preferably <1 ppb and most preferably below 200 nm wavelength transmitting barium fluoride elements with a lead ppb excitation level less than 1 ppb by weight. The invention includes a below 200 nm wavelength transmitting optical fluoride crystal. The optical fluoride crystal 20 is comprised of barium fluoride having a below 200 nm transmission greater than 99%/cm, preferably 157 nm transmission >99%/cm, and a lead ppb level less than 50 and an absorption coefficient at 200 to 210 nm<0.0017 cm$^{-1}$, more preferably a 203 to 207 run absorption coefficient <0.0017 cm$^{-1}$, and most preferably a 205 nm absorption coefficient <0.0016 cm$^{-1}$. Preferably the lead ppb level is less than 10, more preferably <1 by weight. The lead analysis method of the invention can be utilized throughout the optical fluoride crystal optical element manufacturing process to the end product optical element.

Figure 17:
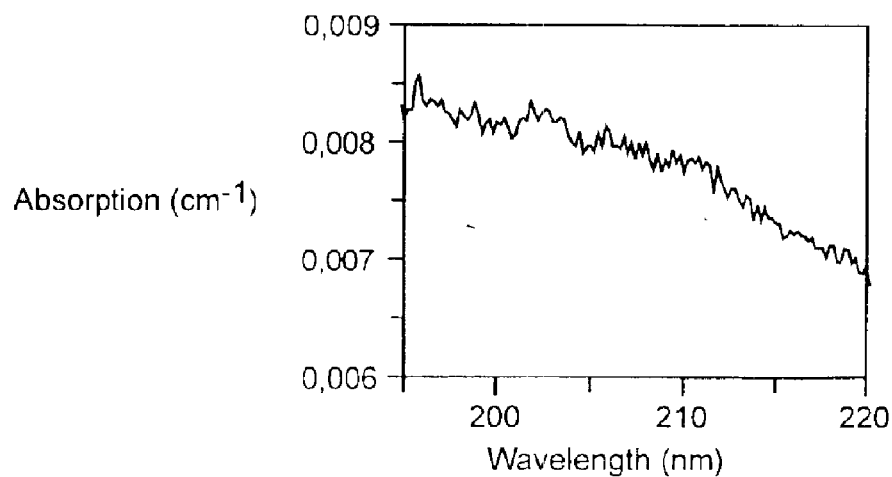
FIG. 17 is an absorption spectrum of an optical fluoride crystal in the spectral range of A-absorption band (200 nm–210 nm) of Pb in accordance with the invention.
Figure 18:
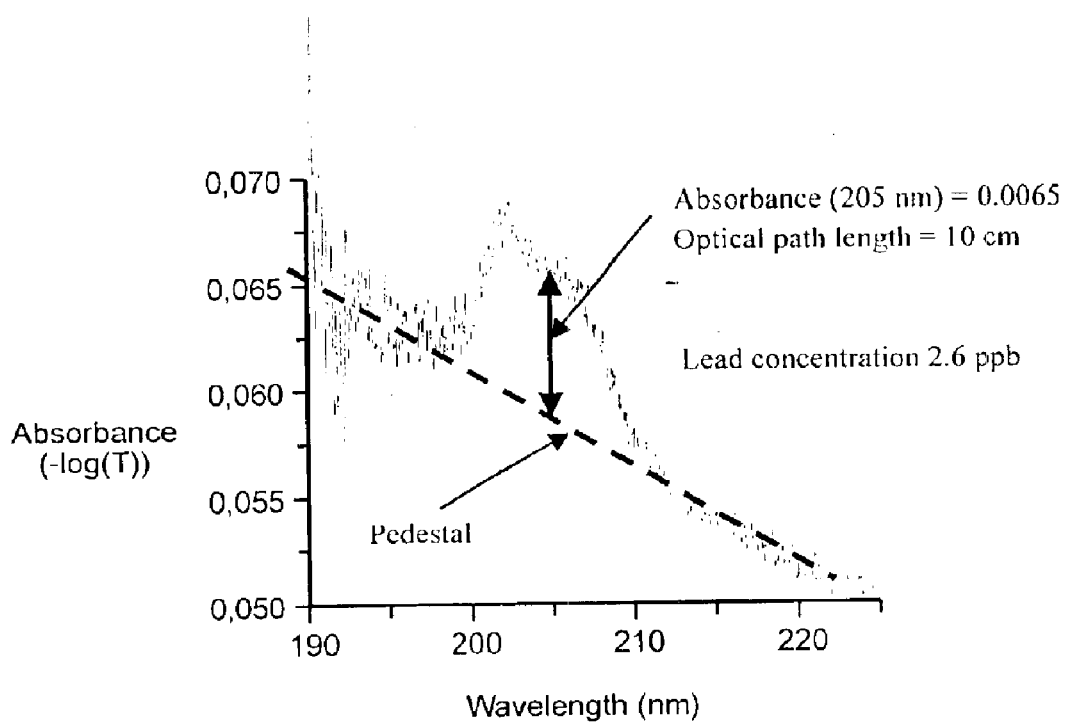
FIG. 18 is a spectrophotometer absorption spectrum of an optical fluoride crystal in accordance with the invention.

The invention includes testing an optical fluoride crystal with reference to its purity relative to lead, by measuring the transmission of the crystal at a given wavelength lying in the range 200 nm to 210 nm, preferably with the wavelength lying in the range 203 nm to 207 nm, and more preferably at a wavelength of 205 nm. Preferably the length of crystal through which the measurement light beam passes is longer than 2 mm, and preferably longer than 1 cm, and more preferably the length of crystal through which the measurement light beam passes is at least 10 cm. Preferably in order to qualify the purity of the crystal under test the method includes comparing the measured transmission value or the absorption coefficient value as calculated from said measured transmission value with a reference value, preferably with the crystal's resulting absorption coefficient compared with 0.0017 cm$^{-1}$. The method includes quantifying the lead content of the crystal under test. Preferably the crystal is selected from alkali fluoride crystals, alkaline-earth fluoride crystals, and mixed combinations of such fluoride crystals, such as NaF, KF, LiF, CaF$_2$, BaF$_2$, MgF$_2$, and SrF$_2$ and mixed combinations thereof In preferred embodiments with measurements on crystals with at least 99 mm light transmission path length (about 100 mm) the method is utilized to provide optical fluoride crystals with lead contaminant level absorption coefficient at 200 to 210 nm (preferably 203 to 207 nm , more preferably about 205 nm )<0.0017 cm$^{-1}$, preferably <0.0016 cm$^{-1}$, preferably <0.0015 cm$^{-1}$, preferably <0.0010 cm$^{-1}$ preferably<0.00085 cm$^{-1}$, preferably <0.0007 cm$^{-1}$, preferably <0.00065 cm$^{-1}$ preferably <0.0004 cm$^{-1}$, preferably <0.0003 cm$^{-1}$, preferably >0.0002 cm$^{-1}$, preferably >0.00025 cm$^{-1}$, preferably in the range of 0.00025 cm$^{-1}$ to 0.0003 cm$^{-1}$. FIG. 17 is an absorption spectrum of an optical fluoride crystal in the spectral range of A-absorption band (200 nm–210 nm) of Pb in accordance with the invention. The optical fluoride crystal sample of FIG. 17 was a calcium fluoride crystal sample with a 50 mm light transmission path length. The optical fluoride crystal sample of FIG. 18 was a calcium fluoride crystal sample with a 10 cm light transmission path length. FIG. 18 illustrates how the pedestal is used in accordance with the invention for detecting very low levels of lead contamination with the scanning of wavelengths centered about 205 nm utilizing a scanning range of about 195–220 nm to identify the pedestal magnitude at 205 nm. In FIG. 18 is seen that the absorbence of lead (0.0065) is nearly 10 times less than the pedestal magnitude at 205 nm. In FIG. 18 the pedestal consists of surface losses and some other internal absorption, with the scanning of 195–200 nm aiding in correctly measuring the 205 nm lead absorbency. Because on the basis of signal to noise ratio it is seen that lead absorbency of about 0.002 is a minimum absorbency. For the sample light transmission path length 10 cm with the minimum absorption coefficient, which can be measured is 0.002/10 cm=0.0002 cm$^{-1}$. Taking into account extinction coefficient δ=0.25 cm$^{-1}$/ppb this absorption coefficient corresponds to lead concentration of about 1 ppb. In FIG. 18 the absorbency at 205 nm is 0.0065 for the 10 cm light transmission path length to give an absorption coefficient of (0.0065/10 cm=0.00065 cm$^{-1}$) 0.00065 cm$^{-1}$. With the 0.00065 cm$^{-1}$ absorption coefficient the measured lead concentration is 2.6 ppb [(0.00065 cm$^{-1}$)(1 ppm lead/0.25 cm$^{-1}$)=2.6 ppb lead].

EXAMPLES

The invention will be further clarified by the following examples.

In practicing the invention a 200–210 nm spectrometer 22, such as a Perkin-Elmer Lambda-900spectrophotometer (PerkinElmer Analytical Instruments, 710 Bridgeport Avenue Shelton, Conn. 06484-4794 USA, Phone: 203-925-4600, 800-762-4000, (+1) 203-762-4000) is utilized. In an embodiment the light source 24 is comprised of a xenon arc lamp. In a preferred embodiment the light source 24 is comprised of a deuterium lamp. Preferably the invention provides for nondestructive nondissolution nonconsuming testing (compared to consuming destructive testing such as by wet chemistry steps and ICP-AES). In an embodiment the invention includes removing a crystal sample with polished faces (preferably at least 50 mm long with faces parallelism better than 1 degree) from a larger crystal ingot body. A measurement size sample piece is cut and polished and inserted into the 200–210 nm spectrometer for measurement therein. The invention provides for calcium fluoride crystals with well below 100 ppb lead concentrations, preferably below 1 ppb based on 200–210 nm transmission measurements. Preferably the invention provides a below 200 nm wavelength transmitting optical fluoride crystal of calcium fluoride having a below 200 nm transmission greater than 99%/cm at 157 nm, a Na by weight impurity level less than 0.5 ppm, a K by weight impurity level less than 0.5 ppm, and a lead ppb level less than 10 by 200–210 nm spectrometer measurement with an absorption coefficient at 200 to 210 nm<0.0017 cm$^{-1}$.

This invention provides for controlling crystal quality of fluoride crystals for use in applications at wavelength <200 nm by measuring fluoride crystal lead impurity absorption in the range between 200 and 210 nm. Fluoride crystals exhibit excellent properties as optical materials for application at wavelength <200 nm because of their high transmission characteristics. But this is true only particularly for crystals free of oxygen impurity. Specifically, the transmission of fluoride crystals at wavelengths 193 and 157 nm (radiation of ArF and F$_2$ lasers correspondingly) can be sufficiently reduced when oxygen species are present in crystals. In order to obtain fluoride crystal with excellent transmission characteristics it is preferred to add scavengers to remove oxygen species from the crystal raw material, such as a lead fluoride scavenger. A lead fluoride scavenger can effectively remove O, but lead element Pb can remain in the crystal after scavenging. Lead impurity has an adverse influence on the crystal transmission characteristics at wavelengths <200 nm. In particular, transmission at 157 nm degrades drastically when lead impurity is present in a crystal.

Qualification of manufactured crystals by measuring the internal transmission at 193 and 157 nm is a complicated procedure requiring a moisture-free spectrophotometer by applying purging or vacuum and special cleaning of sample surfaces. Such procedures raise the cost of crystal manufacturing. We propose to control fluoride crystals in respect of their transmission at wavelengths below 200 nm by measuring Pb absorption above 200 nm, preferably between 200 and 210 nm, with a detection limit of 1 ppb when sample path length is preferably at least about 100 mm. Fluoride crystals, specifically alkali-earth fluorides doped by Pb are characterized by three absorption bands: A (200–210 nm), B (160–170 nm) and C (150–160 nm). These bands are attributed to electron transitions from Pb$^{2+}$ ions ground state $^1S_0$ to excited states $^3P_1$, $^3P_2$ and $^1P_1$ correspondingly. In accordance with our invention we quality control fluoride crystals by measuring Pb absorption/transmission into its A-absorption band (200–210 nm). We have found that the absorption coefficient of Pb at C-band maximum (155 nm) is approximately 2.5 times higher than absorption coefficient at A-band maximum (205 nm). Basing on this relationship we can obtain extinction coefficient for C-band at 155 nm which is $\epsilon(155)=6.25*10^{-4}$ cm$^{-1}$/ppb. For comparison Pb may also be analyzed by ICP-AES. However this method requires "wet chemistry" steps contaminating the sample, and the detection limit of this method doesn't exceed 1 ppm.

Preferably to provide optical element fluoride crystal transmission >99.0%/cm at 157 nm the absorption coefficient of Pb between 200 and 210 nm should be <0.0017 cm$^{-1}$ (base 10).

The invention provides optical fluoride crystal information in regards to the average Pb concentration along sample path length.

The invention provides a method of testing and making a high quality optical fluoride crystal of high purity and excellent optical properties below 200 nm and with low lead levels. The invention provides for the making of optical fluoride crystals such as calcium fluoride with both low lead and oxide contaminants, and the making of below 200 nm transmitting optical fluoride crystal elements for transmission of ArF and F$_2$ laser wavelengths (respective wavelengths of 193 nm and 157 nm), preferably making of such utilizing lead fluoride as an fluorination agent oxide scavenger while still resulting in an optical fluoride crystal and optical element thereof with low lead contamination. The optical fluoride crystals of the invention have below 200 nm (such as 193 and 157 nm) transmission greater than 99% per centimeter (cm$^{-1}$) and are preferably utilized as below 200 nm optical elements such as lithography and laser optics, prisms, projection systems, and illumination systems. The optical fluoride crystals of the invention preferably include crystals of LiF, NaF, CaF$_2$, SrF$_2$, BaF$_2$, and MgF$_2$ and mixed crystals thereof particularly mixed crystals of CaF$_2$ and SrF$_2$, and most preferably unmixed crystals of pure CaF$_2$ or BaF$_2$ or SrF$_2$. In a preferred embodiment of the invention, fluorination agent oxide scavenger compounds such as PbF$_2$ are used in the making of the optical fluoride crystal to reduce the number of sites in the crystal containing oxygen. Although beneficial as lead fluoride to remove oxygen and improve optics below 200 nm, lead is an impurity that is particularly undesirable in fluoride crystals when they are used at wavelengths shorter than 200 nm. Lead-contaminated crystals can suffer particular from a severe reduction in transmission at 157 nm and they absorb at wavelengths shorter than 200 nm when exposed to radiation from lasers of the ArF and F$_2$ excimer type.

Present test methods for evaluating the purity of crystals relative to lead consist in measuring the transmission induced absorption (or laser hardness) of the crystals at wavelengths of 157 nm and/or 193 nm, which are the wavelengths at which such crystals are used. Those measurements are difficult to implement. At such wavelengths shorter than 200 nm, samples must be protected from air and moisture. This makes it necessary either for the chamber containing the sample to be purged or kept under a high vacuum, or else for the entire test apparatus should be maintained in an environment that is free from air and moisture. Furthermore, those prior methods of testing laser hardness are expensive because of the cost of the excimer laser equipment itself and because of the cost of running and maintaining a below 200 nm excimer laser, and as such are not suitable for economic use in the industrial setting of an optical fluoride crystal manufacturing system. Proposals have also been described in Japanese patent application JP-A-2000 119 098 in the name of Nikon Corporation for analyzing the quantity of lead by a method of analyzing trace elements by induction-coupled plasma (ICP) technique. However that method requires wet chemistry steps that risk contaminating the sample. The measuring instrument must be calibrated using induction-coupled plasma standards, which likewise run the risk of becoming contaminated, thereby degrading measurement quality. In any event, the large number of steps involved leaves room for operator error and instrument drift. Furthermore, since lead can be distributed through a crystal, it is necessary to perform analysis at several points. With that type of method, the lead impurity detection limit is no better than one part per million (ppm). The invention provides a new method of testing a fluoride crystal for purity relative to lead, that is particularly useful in the manufacturing of optical fluoride crystals and optical elements therefrom. The invention provides a test that is reliable and easy to implement. The present invention includes shifting the wavelength away from the wavelengths of use (157 nm and/or 193 nm) towards wavelengths in the range 200 nm to 210 nm, preferably in the range 203 nm to 207 nm, and more preferably still of 205 nm.

The inventive making of below 200 nm transmitting optical fluoride crystal elements includes measuring optical fluoride crystal transmission in the range 200 nm to 210 nm. This measured transmission is correlated (proportional) to the transmission at the below 200 nm wavelengths of use (157 nm and/or 193 nm) which is not itself measured and preferably avoided particularly in view of costs and complications for below 200 nm excimer laser exposure. Unexpectedly, it has been found that transmission at a wavelength lying in the range 200 nm to 210 nm makes it possible to detect the presence of lead and to quantify the lead content in crystals of this type with excellent accuracy and precision.

Figure 14:
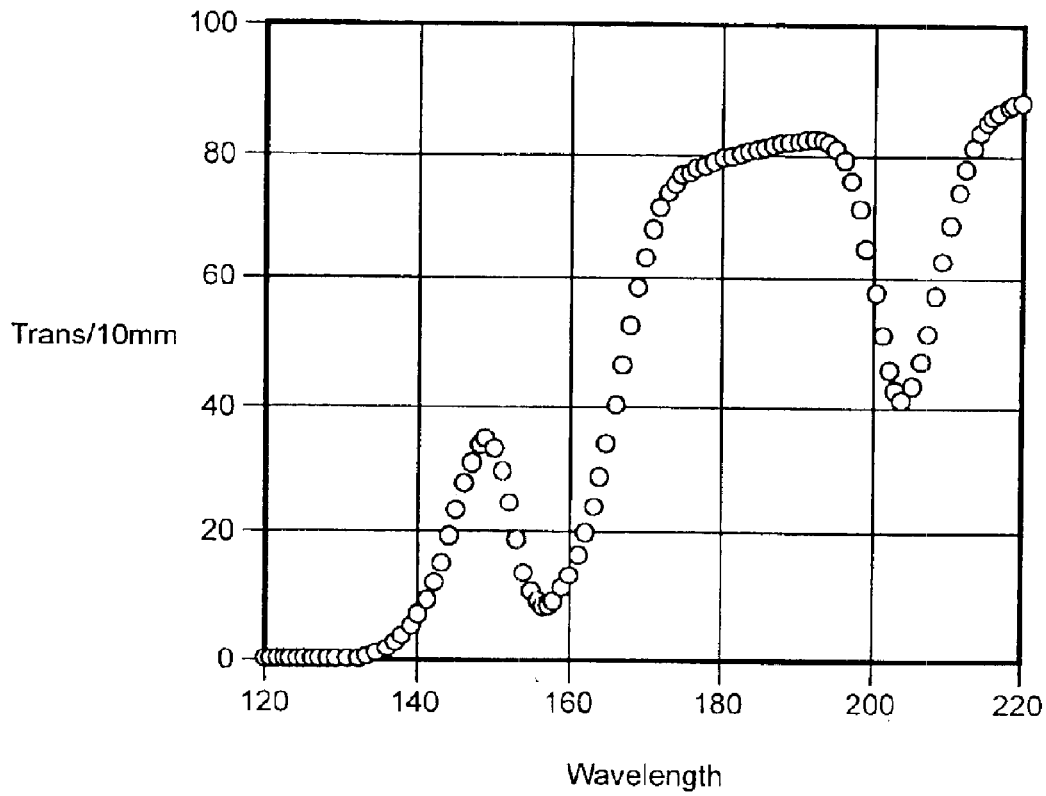
FIG. 14 is a transmission spectrum of an optical fluoride crystal in accordance with the invention (Transmission/10 mm versus 120 to 220 Wavelength).

In accordance with the invention, FIG. 14 is the transmission spectrum of a lead-doped $BaF_2$ crystal in the range 120 nm to 220 nm. This spectrum shows that the absorption coefficient of the lead-polluted crystal at 157 nm is, unexpectedly, about three times greater than that measured in the range 200 nm to 210 nm. Generalizing the ratio of the absorption coefficient of the lead-polluted crystal as measured at 157 nm to the absorption coefficient of the lead-polluted crystal as measured in the range 200 nm to 210 nm to optical fluoride crystals in general, the inventors have found that the value of this ratio lies in the range 2.5 to 3. This value provides correlation between the transmission value of the optical fluoride crystal at the testing measurement wavelengths (200 nm to 210 nm) and the transmission value of said crystal at its wavelengths of use (157 nm and/or 193 nm), with the transmission values being, unexpectedly, of the same order of magnitude. Taking the worse case situation for calculation purposes (putting said ratio at a value of 2.5), in accordance with the invention it is necessary to obtain an absorption coefficient of less than 0.0017 $cm^{-1}$ at a wavelength lying in the range 200 nm to 210 nm in order to obtain transmission greater than 99% per cm at a wavelength of 157 nm (the lithography/laser conditions of use for the crystal under test). The test of the present invention has the advantage of being suitable for performance in air on standard spectrophotometric measurement apparatus operating at wavelengths in the UV region.

Figure 15:
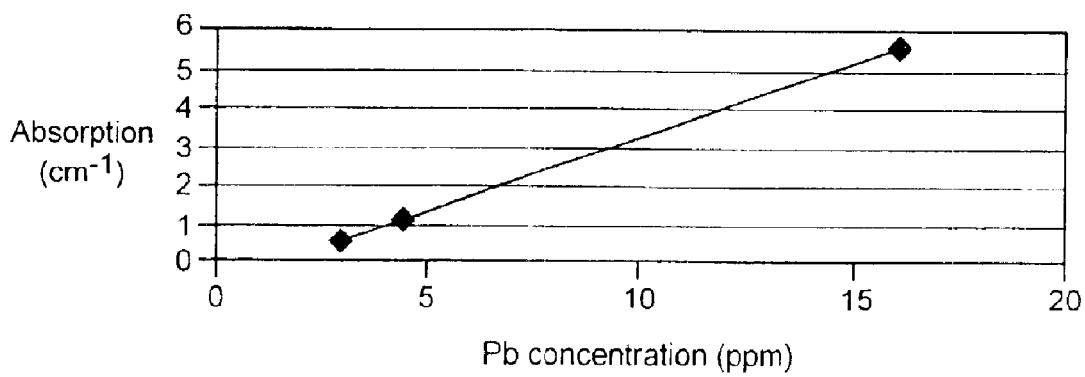
FIG. 15 is a plot of Pb Absorption (cm$^{-1}$) at 205 nm versus Pb concentration (ppm) of optical fluoride crystals in accordance with the invention.

Unexpectedly, the invention also makes it possible to increase the accuracy with which lead impurity is measured and the ability to make high optical quality optical fluoride crystal elements with low lead and absorption coefficient of less than 0.0017 $cm^{-1}$ at a wavelength lying in the range 200 nm to 210 nm. In order to obtain the proportionality factor between the transmission value obtained at the test wavelengths (in the range 200 nm to 210 nm) and the values obtained at the wavelengths of use (157 nm and 193 nm), the inventors have used a wavelength of 205 nm to measure the absorption of $CaF_2$ crystals containing various concentrations of lead impurity (FIG. 15). These measurements show that the extinction coefficient of lead is about 0.30 $cm^{-1}$/ppm of lead for such a $CaF_2$ crystal. The detection limit of the present invention is of parts per billion (ppb) order for lead in optical fluoride crystals. At 157 nm, 1 ppb corresponds to absorption of 0.0003 $cm^{-1}$; which corresponds to transmission of 0.1%/cm, which is a level of loss that can be detected by standard spectrophotometry. We have found that the detection limit of the test for lead contaminant level in the optical fluoride crystal is improved by increasing the path length of the optical fluoride crystal sample through which the light beam passes. In preferred embodiments of the invention, a optical fluoride crystal path length of at least 2 millimeters (mm), and preferably not less than 1 cm, and more preferably at least 10 cm, is utilized for the transmission absorption coefficient testing at the test wavelengths in the range 200 nm to 210 nm.

Figure 16:
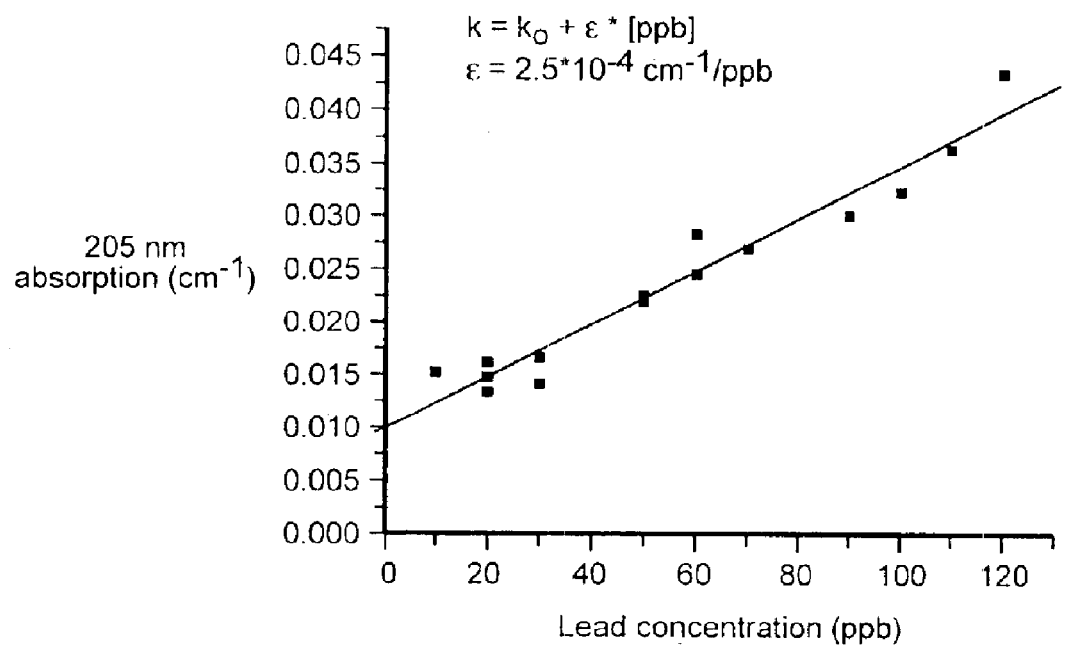
FIG. 16 is a plot of 205 nm Absorption (cm$^{-1}$) versus lead concentration (ppb) of optical fluoride crystals in accordance with the invention.

We have found that in $CaF_2$ samples containing Pb more than 1 ppb, concentration of Pb can be determined based on absorption data in the range 200–210 nm. We confirm this result by data in FIG. 16, where Pb absorption at wavelength 205 nm is plotted versus Pb content (chemical analysis data) for the set of $CaF_2$ samples. From the slope of this linear dependence we obtain $\epsilon(205)=2.5*10^{-4}$ $cm^{-1}$/ppb. It, should be noted that in order to evaluate Pb content in the range from 1 to 10 ppb, the sample length along optical path pass is preferably to be not less than 100 mm.

An implementation of this new test method is qualification of a fluoride crystal relative to its transmission quality at its wavelengths of use, i.e. at 157 nm and/or 193 nm (by comparing the measured transmission value, or the absorption coefficient value as calculated from said measured transmission value, with a reference value). Such qualification is performed at a wavelength lying in the range 200 nm to 210 nm, and the resulting absorption coefficient is advantageously compared with $1.7\times10^{-3}$ $cm^{-1}$; if the measured value is less than this value, then the transmission of the crystal is greater than 99% at 157 nm. In accordance with the invention the test method is utilized as a quality control in the making of below 200 nm transmitting optical elements and optical fluoride crystals. In a further implementation of this test method in accordance with the invention is quantifying the lead impurity level present in the optical fluoride crystal material throughout the crystal manufacturing in an economically feasible manner. The invention can be used to measure lead concentrations in optical fluoride crystals as low as parts per billion. Such quantification is performed by measuring the transmission of the crystal at a wavelength lying in the range 200 nm to 210 nm, preferably in the range 203 nm to 207 nm, and more preferably centered at about 205 nm (205±1 nm, more pref. 205±0.5 nm). The measured transmission above 200 nm makes it possible to determine the lead content by using a suitable reference chart. The test method of the invention is particularly suitable for implementation on optical fluoride crystals selected from alkali fluoride crystals, alkaline-earth fluoride crystals, and mixed combinations of such fluoride crystals. This test method is preferably implemented on crystals of NaF, KF, LiF, $CaF_2$, $BaF_2$, $MgF_2$, and $SrF_2$ and mixed combinations thereof. By way of example, mixed combinations thereof comprise combinations having the formulation $(M1)_x(M2)_{1-x}F_2$ where M1 and M2 are selected independently from Ba, Ca, or Sr and where x is such that $0 \leq x \leq 1$, combinations having the formulation $Ca_{1-x}Ba_xSr_yF_2$ in which x and y are such that $0 \leq x \leq 1$ and $0 \leq y \leq 1$, and also combinations having the formulation $MRF_3$ where M can be selected from Li, Na, or K and R can be selected from Ca, Sr, Ba, or Mg.

The invention is described above with reference to the accompanying figures, in which FIG. 14 shows the transmission spectrum (in the range 120 nm to 220 nm) of a $BaF_2$ crystal polluted with lead; and FIG. 15 shows variations in absorption ($cm^{-1}$) at 205 nm through $CaF_2$ crystals containing various quantities of Pb (in ppm).

It will be apparent to those skilled in the art that various modifications and variations can be made to the present invention without departing from the spirit and scope of the invention. Thus it is intended that the present invention cover the modifications and variations of this invention provided they come within the scope of the appended claims and their equivalents.

What is claimed is:

1. A method of detecting a low lead impurity level in a below 200 nm transmitting optical fluoride crystal said method comprising:

providing a below 200 nm wavelength transmitting optical fluoride crystal having a crystal light transmission path length, said below 200 nm wavelength transmitting optical fluoride crystal light transmission path length $\geq 2$ mm, providing a light transmission spectrophotometer having a light source for producing a transmission test wavelength in the range 200 to 210 nm and a transmission detector for measuring transmission of said test wavelength, transmitting said transmission test wavelength in the range 200 to 210 nm through said below 200 nm wavelength transmitting optical fluoride crystal light transmission path length and measuring the transmission of said 200 to 210 nm test wavelength through said path length to provide a lead ppb impurity level measurement less than 900 ppb.

2. A method as claimed in claim 1 wherein said light source is a lamp.

3. A method as claimed in claim 1, wherein transmitting said transmission test wavelength in the range 200 to 210 nm comprises transmitting a 203 to 207 nm transmission test wavelength in the range 203 to 207 nm through said below 200 nm wavelength transmitting optical fluoride crystal light transmission path length and measuring the transmission of said 203 to 207 nm test wavelength through said path length to provide a lead ppb impurity level measurement less than 500 ppb.

4. A method as claimed in claim 1, wherein transmitting said transmission test wavelength in the range 200 to 210 nm comprises transmitting an about 205 nm transmission test wavelength through said below 200 nm wavelength transmitting optical fluoride crystal light transmission path length and measuring the transmission of said about 205 nm test wavelength through said path length to provide a lead ppb impurity level measurement less than 300 ppb.

5. A method as claimed in claim 1, wherein providing a below 200 nm wavelength transmitting optical fluoride crystal having a crystal light transmission path length $\geq 2$ mm comprises providing a crystal light transmission path length $\geq 1$ cm and transmitting said transmission test wavelength through said $\geq 1$ cm fluoride crystal light transmission path length to provide a lead ppb impurity level measurement less than 100 ppb.

6. A method as claimed in claim 1, wherein providing a below 200 nm wavelength transmitting optical fluoride crystal having a crystal light transmission path length $\geq 2$ mm comprises providing a crystal light transmission path length $\geq 10$ cm and transmitting said transmission test wavelength through said $\geq 10$ cm fluoride crystal light transmission path length to provide a lead ppb impurity level measurement less than 50 ppb.

7. A method of measuring below 1 ppm lead impurity levels in an optical fluoride crystal for transmitting below 200 nm wavelength of light, said method comprising:

providing a below 200 nm wavelength transmitting optical fluoride crystal having a crystal light transmission path length, said below 200 nm wavelength transmitting optical fluoride crystal light transmission path length $\geq 1$ cm, providing a 200–210 nm transmission spectrophotometer having a light source for producing a test wavelength in the range 200 to 210 nm and a detector for calculating an absorption coefficient at said test wavelength, transmitting said test wavelength in the range 200 to 210 nm through said below 200 nm wavelength transmitting optical fluoride crystal light transmission $\geq 1$ cm path length and measuring the absorption coefficient at said test wavelength through said $\geq 1$ cm path length to provide a lead contaminant level absorption coefficient <0.0017 cm-1.

8. A method as claimed in claim 7 wherein transmitting said test wavelength in the range 200 to 210 nm comprises transmitting a 203 to 207 nm test wavelength in the range 203 to 207 nm through said below 200 nm wavelength transmitting optical fluoride crystal light transmission $\geq 1$ cm path length and measuring the absorption coefficient at said 203 to 207 nm test wavelength through said $\geq 1$ cm path length to provide a lead contaminant level absorption coefficient <0.0016 cm$^{-1}$.

9. A method as claimed in claim 7 wherein transmitting said test wavelength in the range 200 to 210 nm comprises transmitting an about 205 nm test wavelength through said below 200 nm wavelength transmitting optical fluoride crystal light transmission $\geq 1$ cm path length and measuring the absorption coefficient at said 205 nm test wavelength through said $\geq 1$ cm path length to provide a lead contaminant level absorption coefficient <0.0015 cm$^{-1}$.

10. A method as claimed in claim 7 wherein providing a below 200 nm wavelength transmitting optical fluoride crystal having a crystal light transmission path length $\geq 1$ cm comprises providing a crystal light transmission path length $\geq 10$ cm to provide a lead contaminant level absorption coefficient impurity measurement less than 50 ppb.

11. A method of making a below 200 nm wavelength optical element, said method comprising:

providing a below 200 nm wavelength transmitting optical fluoride crystal having a crystal light transmission path length, said below 200 nm wavelength transmitting optical fluoride crystal light transmission path length $\geq 2$ mm, providing a 200–210 nm light transmission spectrophotometer having a light source for producing a transmission test wavelength in the range 200 to 210 nm and a transmission detector for measuring transmission of said test wavelength, transmitting said transmission test wavelength in the range 200 to 210 nm through said below 200 nm wavelength transmitting optical fluoride crystal light transmission path length and measuring the transmission of said 200 to 210 nm test wavelength through said path length to provide a contaminant level measurement less than 100 ppb forming the optical fluoride crystal into a below 200 nm wavelength optical element having an absorption coefficient at 200 to 210 nm<0.0017 cm$^{-1}$.

12. A method as claimed in claim 11, wherein providing a below 200 nm wavelength transmitting optical fluoride crystal having a crystal light transmission path length $\geq 2$ mm comprises providing a below 200 nm wavelength transmitting optical fluoride crystal having a crystal light transmission path length $\geq 1$cm and transmitting a 203 to 207 nm test wavelength in the range 203 to 207 nm through said below 200 nm wavelength transmitting optical fluoride crystal light transmission $\geq 1$ cm path length and measuring the absorption coefficient at said 203 to 207 nm test wavelength through said ≧1 cm path length to provide a lead contaminant level measurement less than 50 ppb and forming the optical fluoride crystal into a below 200 nm wavelength optical element having a an absorption coefficient at 203 to 207 nm<0.0016 cm$^{-1}$.

13. A method as claimed in claim 11, wherein providing a below 200 nm wavelength transmitting optical fluoride crystal having a crystal light transmission path length ≧2 nm comprises providing a below 200 nm wavelength transmitting optical fluoride crystal having a crystal light transmission path length ≧10 cm and transmitting an about 205 nm test wavelength through said below 200 nm wavelength transmitting optical fluoride crystal light transmission ≧10 cm path length and measuring the absorption coefficient at about 205 nm through said ≧10 cm path length to provide a lead contaminant level measurement less than 20 ppb and forming the optical fluoride crystal into a below 200 nm wavelength optical element having an absorption coefficient at 205 nm<0.0016 cm$^{-1}$.

14. A method as claimed in claim 11 wherein providing a below 200 nm wavelength transmitting optical fluoride crystal comprises providing a calcium fluoride crystal.

15. A method as claimed in claim 11 wherein providing a below 200 nm wavelength transmitting optical fluoride crystal comprises providing a barium fluoride crystal.

16. A method of making a below 200 nm wavelength transmitting optical fluoride crystal, said method comprising:
providing a premelt calcium fluoride crystal solid,
melting said premelt calcium fluoride crystal solid to form a calcium fluoride melt and growing a calcium fluoride crystal from said melt to provide an optical calcium fluoride crystal for transmitting below 200 nm wavelengths,
providing a light transmission spectrophotometer having a light source for producing a transmission test wavelength in the range 200 to 210 nm and a transmission detector for measuring transmission of said test wavelength and measuring a lead contaminant level in a calcium fluoride path length with said transmission test wavelength in the range 200 to 210 nm, with said grown optical calcium fluoride crystal for transmitting below 200 nm wavelengths having a an absorption coefficient at 200 to 210 nm<0.0017cm$^{-1}$.

17. A method as claimed in claim 16, wherein measuring a lead contaminant level in said calcium fluoride path length with said light transmission 200–210 nm spectrophotometer includes measuring the lead contaminant level in the premelt calcium fluoride crystal solid.

18. A method as claimed in claim 16, wherein measuring a lead contaminant level in calcium fluoride with said light transmission 200–210 nm spectrophotometer includes measuring the lead contaminant level in the calcium fluoride crystal grown from the calcium fluoride melt.

19. A method as claimed in claim 16, wherein said grown optical calcium fluoride crystal for transmitting below 200 nm wavelengths has an absorption coefficient at 200 to 210 nm<0.0016 cm$^{-1}$.

20. A method as claimed in claim 16, wherein said grown optical calcium fluoride crystal for transmitting below 200 nm wavelengths has an absorption coefficient at 203 to 207 nm<0.0017 cm$^{-1}$.

21. A method as claimed in claim 16, wherein said grown optical calcium fluoride crystal for transmitting below 200 nm wavelengths has an absorption coefficient at 205 nm<0.0017 cm$^{-1}$.

22. A below 200 nm wavelength transmitting optical fluoride crystal, said optical fluoride crystal comprised of calcium fluoride having a below 200 nm transmission greater than 990%/cm and a lead ppb level less than 50 and a lead contaminant level absorption coefficient at 200 to 210 nm<0.0017 cm$^{-1}$.

23. An optical fluoride crystal as claimed in claim 22, said calcium fluoride crystal having a 203 to 207 nm lead contaminant level absorption coefficient <0.0017 cm$^{-1}$.

24. An optical fluoride crystal as claimed in claim 22, said calcium fluoride crystal having a 205 nm lead contaminant level absorption coefficient <0.0016 cm$^{-1}$.

25. A method of making a below 200 nm wavelength transmitting optical fluoride crystal, said method comprising:
providing a premelt barium fluoride crystal solid,
melting said premelt barium fluoride crystal solid to form a barium fluoride melt and growing a barium fluoride crystal from said melt to provide an optical barium fluoride crystal for transmitting below 200 nm wavelengths,
providing a light transmission spectrophotometer having a light source for producing a transmission test wavelength in the range 200 to 210 nm and a transmission detector for measuring transmission of said test wavelength and measuring a lead contaminant level in a barium fluoride path length with said transmission test wavelength in the range 200 to 210 nm, with said grown optical barium fluoride crystal for transmitting below 200 nm wavelengths having an absorption coefficient at 200 to 210 nm<0.0017cm$^{-1}$.

26. A method as claimed in claim 25, wherein measuring a lead contaminant level in said barium fluoride path length with said light transmission spectrophotometer includes measuring the lead contaminant level in the premelt barium fluoride crystal solid.

27. A method as claimed in claim 25, wherein measuring a lead contaminant level in barium fluoride with said light transmission spectrophotometer includes measuring the lead contaminant level in the barium fluoride crystal grown from the barium fluoride melt.

28. A method as claimed in claim 25, wherein said grown optical barium fluoride crystal for transmitting below 200 nm wavelengths has an absorption coefficient at 200 to 210 nm<0.0016 cm$^{-1}$.

29. A method as claimed in claim 25, wherein said grown optical barium fluoride crystal for transmitting below 200 nm wavelengths has an absorption coefficient at 203 to 207 nm<0.0017 cm$^{-1}$.

30. A method as claimed in claim 25, wherein said grown optical barium fluoride crystal for transmitting below 200 nm wavelengths has an absorption coefficient at 205nm<0.0017 cm$^{-1}$.

31. A below 200 nm wavelength transmitting optical fluoride crystal, said optical fluoride crystal comprised of barium fluoride having a below 200 nm transmission greater than 99%/cm and a lead ppb level less than 50 and a lead contaminant level absorption coefficient at 200 to 210 nm<0.0017 cm$^{-1}$.

32. An optical fluoride crystal as claimed in claim 31, said barium fluoride crystal having a 203 to 207 nm lead contaminant level absorption coefficient <0.0017 cm$^{-1}$.

33. An optical fluoride crystal as claimed in claim 31, said barium fluoride crystal having a 205 nm lead contaminant level absorption coefficient <0.0016 cm$^{-1}$.

* * * * *